US010472683B2

(12) United States Patent
Zylberberg et al.

(10) Patent No.: US 10,472,683 B2
(45) Date of Patent: Nov. 12, 2019

(54) **DETECTION OF *MYCOPLASMA* IN CELL CULTURES AND CELL CULTURE DERIVED BIOLOGICALS**

(71) Applicants: Akron Biotechnology, LLC, Boca Raton, FL (US); Juan Manuel Rodriguez, Buenos Aires (AR); Andres Clemente Hernando Insua, Buenos Aires (AR); Ricardo Ariel Lopez, Autonomous City of Buenos Aires (AR)

(72) Inventors: Claudia Zylberberg, Delray Beach, FL (US); Juan Manuel Rodriguez, Buenos Aires (AR); Andres Clemente Hernando Insua, Buenos Aires (AR); Ricardo Ariel Lopez, Autonomous City of Buenos Aires (AR)

(73) Assignee: Akron Biotechnology, LLC., Boca Raton, FL (US)

( * ) Notice: Subject to any disclaimer, the term of this patent is extended or adjusted under 35 U.S.C. 154(b) by 0 days.

(21) Appl. No.: 14/404,902

(22) PCT Filed: May 31, 2013

(86) PCT No.: PCT/US2013/043644
§ 371 (c)(1),
(2) Date: Dec. 1, 2014

(87) PCT Pub. No.: WO2013/181553
PCT Pub. Date: Dec. 5, 2013

(65) Prior Publication Data
US 2015/0111207 A1  Apr. 23, 2015

Related U.S. Application Data

(60) Provisional application No. 61/654,620, filed on Jun. 1, 2012, provisional application No. 61/656,207, filed on Jun. 6, 2012.

(51) Int. Cl.
*C12Q 1/68* (2018.01)
*C07H 21/04* (2006.01)
*C12Q 1/689* (2018.01)

(52) U.S. Cl.
CPC ....... *C12Q 1/689* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

| | | | |
|---|---|---|---|
| 4,563,419 A | 1/1986 | Ranki et al. | |
| 4,851,330 A | 7/1989 | Kohne | |
| 5,432,272 A | 7/1995 | Benner | |
| 5,591,607 A * | 1/1997 | Gryaznov | C07H 19/06 435/6.12 |
| 5,656,427 A * | 8/1997 | Hammond | C12Q 1/689 435/6.12 |
| 6,277,607 B1 * | 8/2001 | Tyagi | C12Q 1/6818 435/5 |
| 6,582,908 B2 * | 6/2003 | Fodor et al. | 506/9 |
| 6,773,882 B2 * | 8/2004 | Hogan | C12Q 1/6895 435/471 |
| 2004/0091935 A1 * | 5/2004 | Doxsey | 435/7.1 |
| 2007/0065828 A1 | 3/2007 | Kim et al. | |
| 2009/0018031 A1 | 1/2009 | Trinklein et al. | |
| 2009/0181368 A1 * | 7/2009 | Iwakiri | C12Q 1/689 435/6.12 |

FOREIGN PATENT DOCUMENTS

WO WO2011153277 12/2011

OTHER PUBLICATIONS

Wang, H. et al, "Simultaneous detection and identification of common cell culture contaminant and pathogenic mollicutes strains by reverse line blot hybridization", Applied Environmental Microbiology, 70:3:1483-1486, especially p. 1484 table 1, (Mar. 2004).
GenBank Accession No. AF443608.1, Mar. 16, 2004.
GenBank Accession No. FJ468427.1, Jan. 13, 2010.
GenBank Accession No. GU905026.1, Apr. 20, 2010.
GenBank Accession No. X58554.1, Oct. 6, 1992.

* cited by examiner

*Primary Examiner* — Katherine D Salmon
(74) *Attorney, Agent, or Firm* — Mintz Levin Cohn Ferris Glovsky and Popeo, P.C.; Nicholas A. Zachariades

(57) ABSTRACT

Sequences having specificity for *Mycoplasma* and related *Mollicutes* genus strains and uses thereof. Methods of use include detection of samples contaminated with *Mycoplasma*. Kits are provided and comprise one or more oligonucleotides for the detection of *Mycoplasma* and related *Mollicutes* genus strains.

7 Claims, 7 Drawing Sheets
Specification includes a Sequence Listing.

In order to build the High Melting Positive Control (a discriminatory positive control), each one of the following nucleotides sequences was cloned into a standard cloning vector (No mater of their orientation: sense or anti sense).

High Melting Positive Control Sequences

SEQ ID No 1
GTCACACCAT GGGAGCTGGT AACCGCCCGG CGTGGGCGGT GCCACCCCTC CCCGTAACAA GGTATCCCTA CGAGAAC
CAGTGTGGTA CCCTCGACCA TTGGCGGGCC GCACCCGCCA CGGTGGGGAG GGGCATTGTT CCATAGGGAT GCTCTTG

SEQ ID No 2
GTCACACCAT GGGAGCTGGT AACGTGGCCG CCCGGCGTGG GCGGTGCCAC CCCTCCCGCC GGCGTAACAA GGTATCCCTA CGAGAAC
CAGTGTGGTA CCCTCGACCA TTGCACCGGC GGGCCGCACC CGCCACGGTG GGGAGGGCGG CCGCATTGTT CCATAGGGAT GCTCTTG

SEQ ID No 3
GTCACACCAT GGGAGCTGGT AACCCTTCGT GGCCGCCCGG CGTGGGCGGT GCCACCCCTC CCGCCGGCGG CCCGTAACAA GGTATCCCTA CGAGAAC
CAGTGTGGTA CCCTCGACCA TTGGGAAGCA CCGGCGGGCC GCACCCGCCA CGGTGGGGAG GGCGGCCGCC GGGCATTGTT CCATAGGGAT GCTCTTG

SEQ ID No 4
GTCACACCAT GGGAGCTGGT AACCGCCCGG CGTGGGCGGT GCCACCCCTC CCCCCGGCGT AACAAGGTAT CCCTACGAGA AC
CAGTGTGGTA CCCTCGACCA TTGGCGGGCC GCACCCGCCA CGGTGGGGAG GGGGGCCGCA TTGTTCCATA GGGATGCTCT TG

SEQ ID No 5
GTCACACCAT GGGAGCTGGT AACCGCCCGG CGTGGGCGGT GCCACCCCTC CCCCCGGCGG CCCGTAACAA GGTATCCCTA CGAGAAC
CAGTGTGGTA CCCTCGACCA TTGGCGGGCC GCACCCGCCA CGGTGGGGAG GGGGGCCGCC GGGCATTGTT CCATAGGGAT GCTCTTG

SEQ ID No 6
GTCACACCAT GGGAGCTGGT AACGTGGCCG CCCGGCGTGG GCGGTGCCAC CCCTCCCCGT AACAAGGTAT CCCTACGAGA AC
CAGTGTGGTA CCCTCGACCA TTGCACCGGC GGGCCGCACC CGCCACGGTG GGGAGGGGCA TTGTTCCATA GGGATGCTCT TG

SEQ ID No 7
GTCACACCAT GGGAGCTGGT AACGTGGCCG CCCGGCGTGG GCGGTGCCAC CCCTCCCCCC GGCGGCCCGT AACAAGGTAT CCCTACAGAGA AC
CAGTGTGGTA CCCTCGACCA TTGCACCGGC GGGCCGCACC CGCCACGGTG GGGAGGGGGG CCGCCGGGCA TTGTTCCATA GGGATGCTCT TG

SEQ ID No 8
GTCACACCAT GGGAGCTGGT AACCCTTCGT GGCCGCCCGG CGTGGGCGGT GCCACCCCTC CCCCCGGCGT AACAAGGTAT CCCTACGAGA AC
CAGTGTGGTA CCCTCGACCA TTGGGAAGCA CCGGCGGGCC GCACCCGCCA CGGTGGGGAG GGGGGCCGCA TTGTTCCATA GGGATGCTCT TG

SEQ ID No 9
GTCACACCAT GGGAGCTGGT AACCCTTCGT GGCCGCCCGG CGTGGGCGGT GCCACCCCTC CCCGTAACAA GGTATCCCTA CGAGAAC
CAGTGTGGTA CCCTCGACCA TTGGGAAGCA CCGGCGGGCC GCACCCGCCA CGGTGGGGAG GGGCATTGTT CCATAGGGAT GCTCTTG

FIGURE 3

Oligonucleotide sequences

Forward Primers

| Seq ID NO | |
|---|---|
| 10 | 5´ GTC AMA CCA TGG GAG YTG GTA A 3´ |
| 11 | 5´ CAA ACC ACG AAA GTG GGC AA 3´ |
| 12 | 5´ CCC GTC AAA CTA CGA GAG GTA AGT A 3´ |
| 13 | 5´ CCG TCA CAC CAT GAG AGT TGA TAA 3´ |
| 14 | 5´ CCG TCA AAC TAT GAA AGC TGG TAA 3´ |

Reverse Primers

| Seq ID NO | |
|---|---|
| 15 | 5´ GTT CTC GTA GGG RTA CCT TGT TAC G 3´ |

FIGURE 4

DETECTION OF *MYCOPLASMA* IN CELL CULTURES AND CELL CULTURE DERIVED BIOLOGICALS

CROSS REFERENCE TO RELATED APPLICATIONS

This is a national stage filing in accordance with 35 U.S.C. § 371 of PCT/US2013/043644, filed May 31, 2013, which claims priority to U.S. provisional patent application No. 61/654,620 filed Jun. 1, 2012 and U.S. Provisional patent application No. 61/656,207 filed Jun. 6, 2012 which are incorporated herein by reference in their entirety.

FIELD OF INVENTION

Embodiments of the invention are directed to compositions for detection of *Mycoplasma* in biological samples, methods of detection and uses thereof.

BACKGROUND

*Mycoplasma* contamination of cell culture systems continues to present major problems for basic research as well as for the manufacturing of bioproducts.

Around 25 percent of cell culture contaminations are due to *Mycoplasma* species. This wall-less bacteria constitutes the smallest self-replicating microorganism and because of their small size they can pass through some filters used to sterilize culture media. *Mycoplasma* infected cells can change physiological, morphological and immunological cell properties. Nowadays, detection of *Mycoplasma* is mandatory for every cell culture laboratory. Mainly, the U.S. Pharmacopoeia and FDA specify that cell culture in pharmaceutical production must be *Mycoplasma*-free.

*Mycoplasma* infection in cell cultures normally is a chronic infection which may not be obvious by visual inspection with light microscopy; consequently, it is crucial to develop effective methodologies to test *Mycoplasma* contaminations periodically. A variety of tests to detect *Mycoplasmas* in cell cultures have been developed (e.g. fluorochrome staining of DNA, monitoring toxic metabolites, culture method, etc.) but each method shows certain disadvantages. The major drawback of those methods is non-specificity or a very time-consuming procedure.

SUMMARY

Embodiments of the invention are directed to, inter alia, isolated and/or synthetic nucleic acid sequences specifically hybridize to the 16S-23S ribosomal RNA intergenic regions of *Mycoplasma* and related *Mollicutes* genus. Further embodiments, include isolated and/or synthetic nucleic acid sequences wherein each oligonucleotide is substantially complementary to a portion of the 16S-23S ribosomal RNA intergenic regions of *Mycoplasma* and related *Mollicutes* genus. In other embodiments, one or more of each of the nucleic acids is specific for at least 5 consecutive nucleic acids of the 16S-23S ribosomal intergenic regions of *Mycoplasma* and/or related *Mollicutes* genus strains in the 5' to 3' and 3' to 5' directions. In some embodiments, the nucleic acids comprise at least five nucleic acids. In some embodiments, the nucleic acids comprise a sequence identity of at least about 50% to about 99.99% to a portion of the 16S-23S ribosomal RNA intergenic regions of *Mycoplasma* and/or related *Mollicutes* genus of either the 5' to 3' or 3' to 5' direction. In yet other embodiments, the nucleic acids specifically detect more than one hundred *Mycoplasma* species (including *Mollicutes* genus such as *Acholeplasma* and *Spyroplasma*). In other embodiments, methods are provided for detection of *Mycoplasma* and related *Mollicutes* genus strains in samples. In other embodiments, kits are provided. Other aspects are described infra.

BRIEF DESCRIPTION OF THE DRAWINGS

FIG. 3 shows the sequences (SEQ ID NOS: 1 to 9) for the High Melting Positive Control (also referred to herein as the discriminatory positive control (DPC)) in either orientation (sense or antisense).

FIG. 4 shows the sequences of the forward (SEQ ID NOS: 10 to 14) and reverse primers (SEQ ID NO: 15) used in the detection of *Mycoplasma* and related *Mollicutes* genus in samples.

DETAILED DESCRIPTION

Figure 1A:
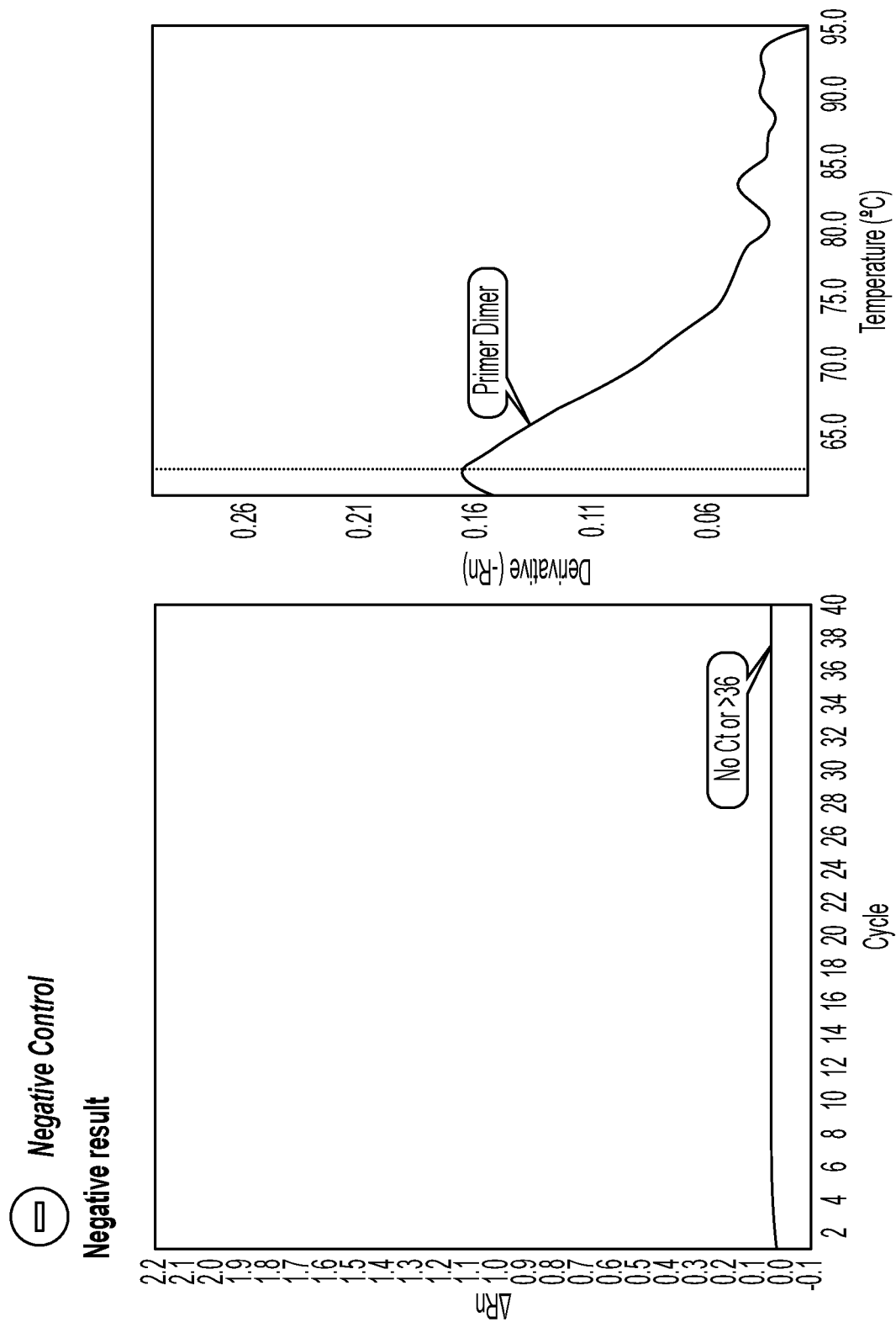
FIG. 1 shows the results of an example of a positive result (validated by controls). The top panel is the negative control, the middle panel is the discriminatory positive control (DPC) and the bottom panel is an unknown sample, showing that the sample was contaminated with *Mycoplasma*.
Figure 1B:
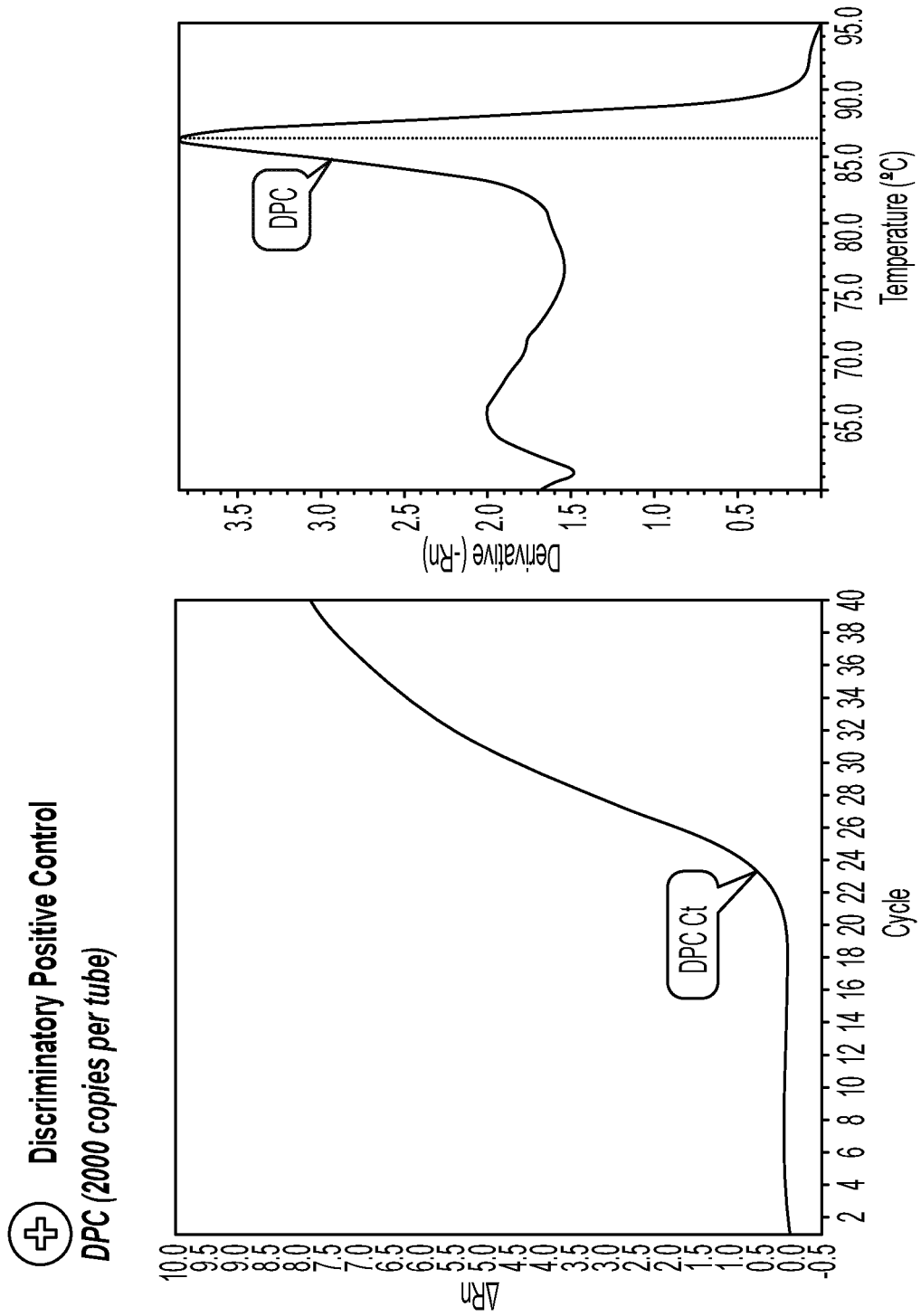
Figure 1C:
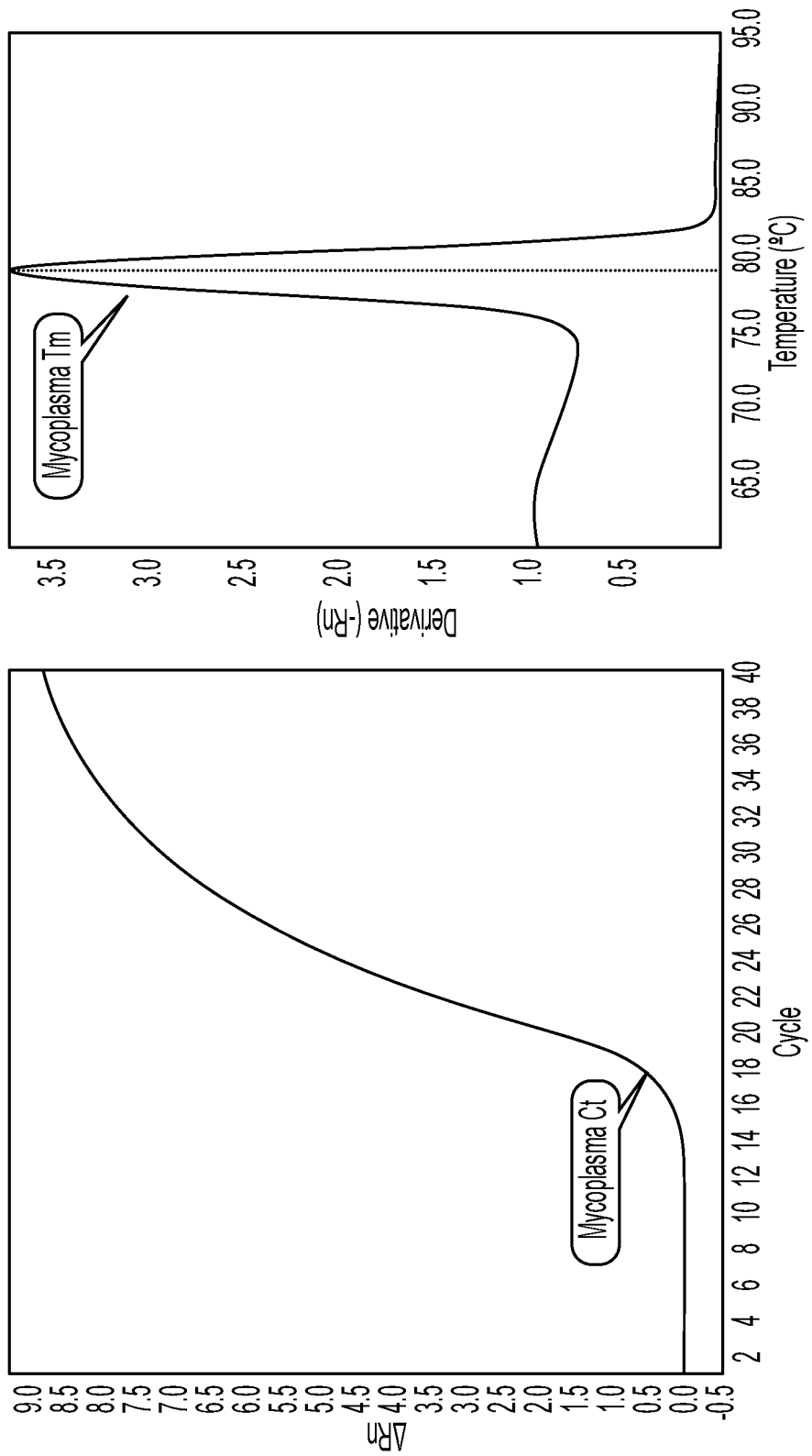
Figure 2A:
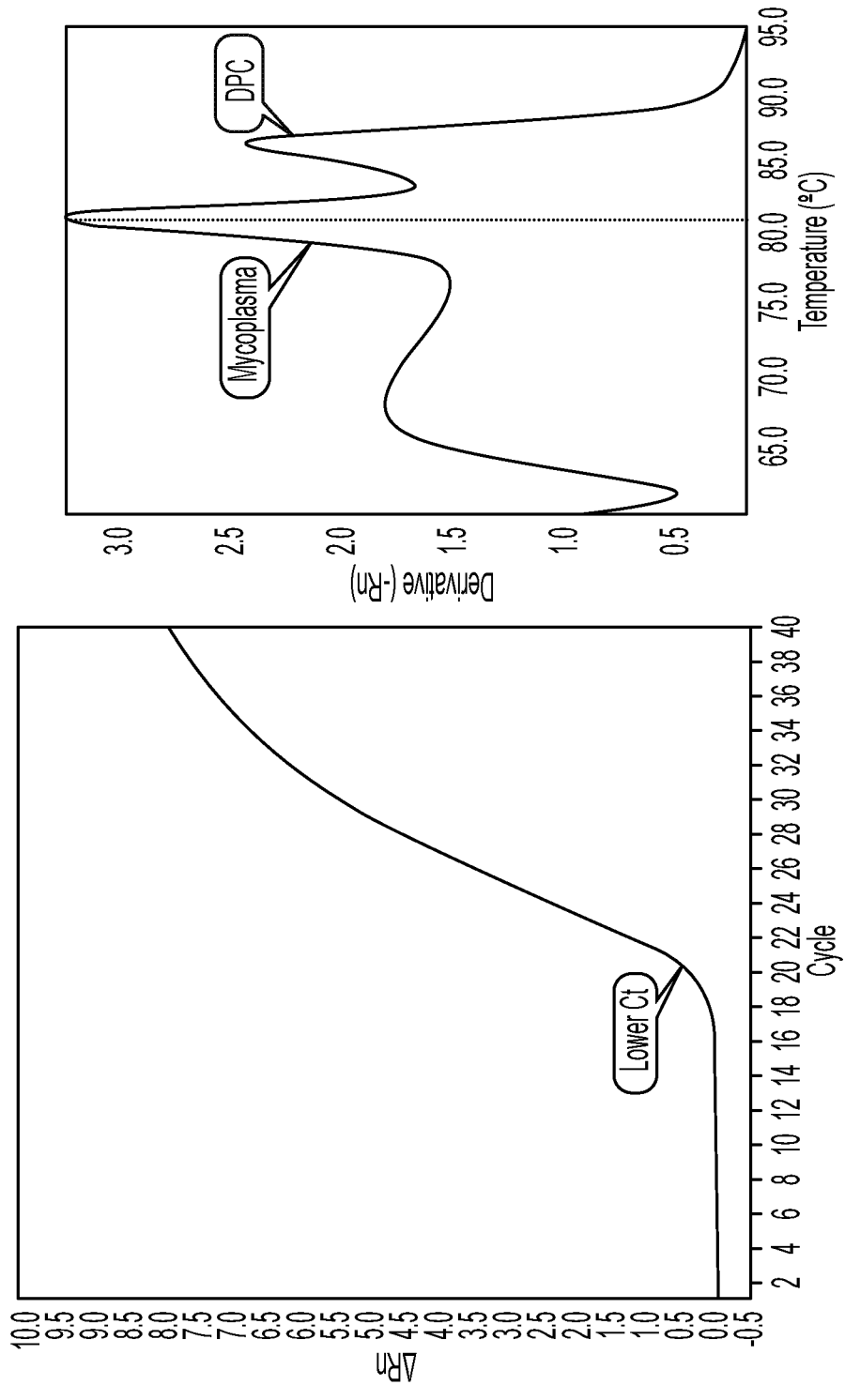
FIG. 2 shows the results from an example of an inhibition control reaction for a heavily (top panel) and a weakly contaminated sample (lower panel).
Figure 2B:
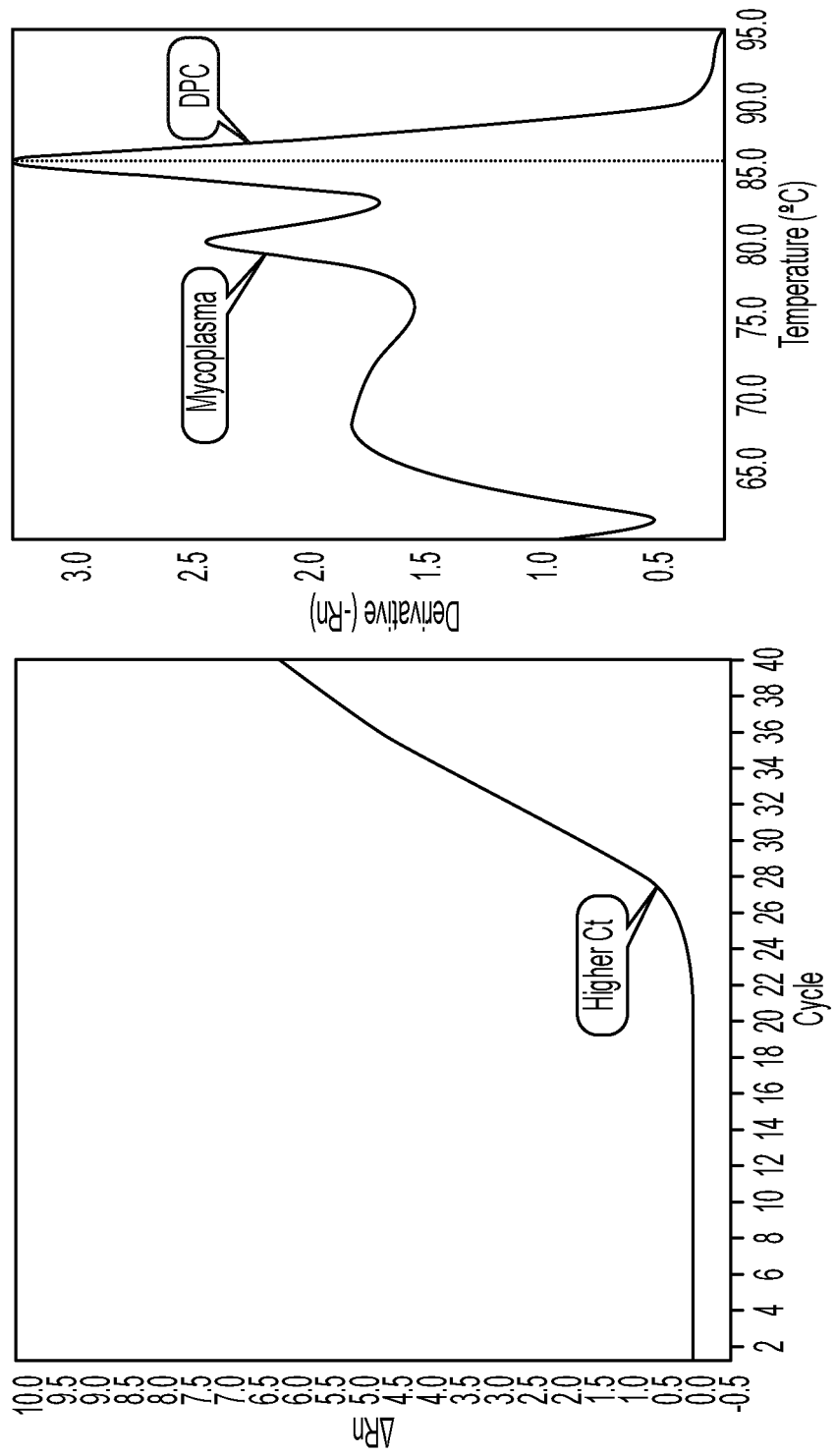

Embodiments of the invention are directed to isolated nucleic acids that detect *Mycoplasma* species, including related species, such as, for example, *Mollicutes* genus, e.g., *Acholeplasma* and *Spyroplasma*. The compositions comprise nucleic acids which specifically hybridize to nucleic acid sequences of the 16S-23S ribosomal RNA intergenic spacer regions of *Mycoplasma* species. In other general embodiments, methods for the detection of *Mycoplasma* in biological samples, e.g. cell cultures, cell culture derived biologicals, are provided.

The methods provided herein are advantageous as compared to other methods currently used in the detection of *Mycoplasma*. The methodologies herein, are specific, sensitive, completely reliable and fast providing accurate results in less than about four hours.

Definitions

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, preferably up to 10%, more preferably up to 5% and more preferably still up to 1% of a given value. Alternatively, particularly with respect to biological systems or processes, the term can mean within an order of magnitude, preferably within 5-fold, and more preferably "within 2-fold, of a value. Where particular values are described in the application and claims, unless otherwise stated the term "about" meaning within an acceptable error range for the particular value should be assumed.

"Sample" is used herein in its broadest sense. A sample comprising polynucleotides, polypeptides, peptides, antibodies and the like may comprise a bodily fluid; cell-derived biologicals, like, for example, a soluble fraction of a cell preparation, or media in which cells were grown; a chromosome, an organelle, or membrane isolated or extracted from a cell; genomic DNA, RNA, or cDNA, polypeptides, or peptides in solution or bound to a substrate; a cell; a tissue; a tissue print; a fingerprint, skin or hair; and the like. The term "sample" is meant to cover the term "biological samples."

"Biological samples" include, tissue cultures, cells (including, transformed, transduced, etc.) solid and body fluid samples. However, the biological samples used in the present invention can include any types of cells, protein or membrane extracts of cells, blood or biological fluids such as ascites fluid or brain fluid (e.g., cerebrospinal fluid). Examples of solid biological samples include, but are not limited to, samples taken from tissues of the central nervous system, bone, breast, kidney, cervix, endometrium, head/neck, gallbladder, parotid gland, prostate, pituitary gland, muscle, esophagus, stomach, small intestine, colon, liver, spleen, pancreas, thyroid, heart, lung, bladder, adipose, lymph node, uterus, ovary, adrenal gland, testes, tonsils and thymus. Examples of "body fluid samples" include, but are not limited to blood, serum, semen, prostate fluid, seminal fluid, urine, saliva, sputum, mucus, bone marrow, lymph, and tears.

An "isolated" biological component (such as a nucleic acid) has been substantially separated or purified away from other biological components in which the component naturally occurs, such as other chromosomal and extrachromosomal DNA, RNA, and proteins. Nucleic acids that have been "isolated" include nucleic acids purified by standard purification methods. The term also embraces nucleic acids prepared by recombinant expression in a host cell as well as chemically synthesized nucleic acids, such as probes and primers, for example *Mycoplasma* and related *Mollicutes* genus strains, specific probes and primers disclosed herein. Isolated does not require absolute purity, and can include nucleic acid molecules that are at least 50% isolated, such as at least 75%, 80%, 90%, 95%, 98%, 99%, or even 100% isolated.

The term "complement" used herein means one strand of a double-stranded nucleic acid, in which all the bases are able to form base pairs with a sequence of bases in another strand. Also, complementary is defined as not only those completely matching within a continuous region of at least 5 contiguous nucleotides, but also those having identity of at least 50%, 70%, 80%, 90%, 95% or higher within that region. Complementary nucleotides are, generally, adenine (a) and thymine (t) or uracil (u), and cytosine (c) and guanine (g). Two single stranded RNA or DNA molecules are said to be substantially complementary when the nucleotides of one strand, optimally aligned and compared and with appropriate nucleotide insertions or deletions, pair with at least 50% of the nucleotides of the other strand, preferably at least 60% of the nucleotides, more preferably at least 70% of the nucleotides, still more preferably, at least 80% of the nucleotides, and still more preferably between 90% and 100% of the nucleotides.

As referred to herein, "fragments of a nucleic acid sequence" or "portions of a nucleic acid sequence" or "portion" comprise at least about 10 or 15 nucleic acid residues (nucleotides), or at least about 20, 30, 40, 50, 60, 70, 80, 90, 100, 150 or 200 nucleic acid residues. Representative examples of oligonucleotide fragments are 2, 3, 4, 5, 6, 7, 8, 9, 10, 11, 12, 13, 14, 15, 16, 17, 18, 19 or 20 nucleotides in length.

The terms "primers", "oligomers" and "oligonucleotides" are used interchangeably herein, and refer to a chain of at least two nucleic acid monomers which can be deoxyribonucleic acids, ribonucleic acids, natural and/or modified monomers or linkages, including deoxyribonucleosides, ribonucleosides, substituted and alpha-anomeric forms thereof, peptide nucleic acids (PNA), locked nucleic acids (LNA), phosphorothioate, methylphosphonate, and the like. The primers may be "chimeric," that is, composed of different regions. In the context of this invention "chimeric" compounds are oligonucleotides, which contain two or more chemical regions, for example, DNA region(s), RNA region(s), PNA region(s) etc. The primers or oligomers can also serve as probes. The primers or oligomers may be synthetic, i.e. designed to detect a desired nucleic acid sequence as embodied herein. These synthetic primers may include various nucleobases (e.g. locked nucleic acids) which confer certain properties, such as hybridizing to a *Mycoplasma* and/or related *Mollicutes* genus strain nucleic acids, under varying conditions, e.g. low stringency conditions. They can have sequence identity of at least about 40% to at least five consecutive nucleobases of a target nucleic acid (e.g. *Mycoplasma* and/or related *Mollicutes* genus strain nucleic acids).

The term "isolated" or "isolating" refers to material, such as a nucleic acid or a protein, which is: (1) substantially or essentially free from components which normally accompany or interact with the material as found in its naturally occurring environment or (2) if the material is in its natural environment, the material has been altered by deliberate human intervention (e.g. may contain one or more mutants, variants, analogs, deletions substitutions, insertion or combinations thereof) to a composition and/or placed at a locus in the cell other than the locus native to the material.

A probe comprises an isolated nucleic acid capable of hybridizing to a target nucleic acid (such as *Mycoplasma* and related *Mollicutes* genus strain nucleic acids, for example a *Mycoplasma* 16S-23S ribosomal intergenic region nucleic acid molecules). A detectable label or reporter molecule can be attached to a probe. Typical labels include radioactive isotopes, enzyme substrates, co-factors, ligands, chemiluminescent or fluorescent agents, haptens, and enzymes.

In the present context, the terms "nucleobase" covers naturally occurring nucleobases as well as non-naturally occurring nucleobases. It should be clear to the person skilled in the art that various nucleobases which previously have been considered "non-naturally occurring" have subsequently been found in nature. Thus, "nucleobase" includes not only the known purine and pyrimidine heterocycles, but also heterocyclic analogues and tautomers thereof. Illustrative examples of nucleobases are adenine, guanine, thymine, cytosine, uracil, purine, xanthine, diaminopurine, 8-oxo-$N^6$-methyladenine, 7-deazaxanthine, 7-deazaguanine, $N^4,N^4$-ethanocytosin, $N^6,N^6$-ethano-2,6-diaminopurine, 5-methylcytosine, 5-($C^3$-$C^6$)-alkynylcytosine, 5-fluorouracil, 5-bromouracil, pseudoisocytosine, 2-hydroxy-5-methyl-4-triazolopyridin, isocytosine, isoguanin, inosine and the "non-naturally occurring" nucleobases described in Benner et al., U.S. Pat. No. 5,432,272. The term "nucleobase" is intended to cover every and all of these examples as well as analogues and tautomers thereof. Especially interesting nucleobases are adenine, guanine, thymine, cytosine, and uracil, which are considered as the naturally occurring nucleobases in relation to therapeutic and diagnostic application in humans. Nucleobases also include the natural nucleosides.

As used herein, "nucleoside" includes the natural nucleosides, including 2'-deoxy and 2'-hydroxyl forms, e.g., as described in Kornberg and Baker, DNA Replication, 2nd Ed. (Freeman, San Francisco, 1992).

"Analogs" in reference to nucleosides includes synthetic nucleosides having modified base moieties and/or modified sugar moieties, e.g., described generally by Scheit, Nucleotide Analogs, John Wiley, New York, 1980; Freier & Altmann, *Nucl. Acid. Res.,* 1997, 25(22), 4429-4443, Toulmé, J. J., *Nature* Biotechnology 19:17-18 (2001); Manoharan M., *Biochemica et Biophysica Acta* 1489:117-139(1999); Freier S. M., *Nucleic Acid Research,* 25:4429-4443 (1997), Uhlman, E., *Drug Discovery & Development,* 3: 203-213 (2000), Herdewin P., *Antisense & Nucleic Acid Drug Dev.,* 10:297-310 (2000),); 2'-O, 3'-C-linked [3.2.0] bicycloarabinonucleosides (see e.g. N. K Christiensen., et al, *J. Am. Chem. Soc.,* 120: 5458-5463 (1998). Such analogs include synthetic nucleosides designed to enhance binding properties, e.g., duplex or triplex stability, specificity, or the like.

The term "wild-type" or "native" is used interchangeably herein and means that the nucleic acid fragment does not comprise any mutations. In an aspect, the term "wild type" or "native" sequence can indicate a starting or reference sequence prior to a manipulation of the invention. A mutant or variant sequence is a sequence showing substantial variation from a wild type or reference sequence that differs from the wild type or reference sequence at one or more positions. A particular nucleic acid sequence also implicitly encompasses "splice variants" and "allelic variants." "Splice variants," are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Any products of a splicing reaction, including recombinant forms of the splice products, are included in this definition.

As used herein, the term "homolog", when used in the context of an oligonucleotide, means an oligonucleotide sharing a common evolutionary ancestor or having at least 50% identity thereto.

The term "target nucleic acid" refers to a nucleic acid (often derived from a biological sample), to which the oligonucleotide is designed to specifically hybridize. It is either the presence or absence of the target nucleic acid that is to be detected, or the amount of the target nucleic acid that is to be quantified. The target nucleic acid has a sequence that is complementary to the nucleic acid sequence of the corresponding oligonucleotide directed to the target. The term target nucleic acid may refer to the specific subsequence of a larger nucleic acid to which the oligonucleotide is directed or to the overall sequence (e.g., gene or mRNA) whose expression level it is desired to detect. The difference in usage will be apparent from context.

As used herein, "specific binding" and "specifically bound" means that the reagent, substance or moiety is a binding pair member that binds or is bound to a desired substance or element with a higher binding affinity and/or specificity to the substance or element than to any other moiety present in the sample or used in the assay method.

As used herein, the terms "hybridize," "hybridizes," and "hybridization" refer to the binding of two or more nucleic acid sequences that are at least 60% (preferably, 70%, 75%, 80%, 85%, 90%, 95%, 98%, 99% or 99.5%) complementary to each other. Nucleic acid hybridization techniques and conditions are known to the skilled artisan and have been described, e.g., in Sambrook et al. Molecular Cloning A Laboratory Manual, 2nd Ed. Cold Spring Lab. Press, (December 1989); U.S. Pat. Nos. 4,563,419 and 4,851,330, and in Dunn, et al., Cell, Vol. 12, pp. 23-26 (1978) among many other publications.

Hybridization conditions resulting in particular degrees of stringency will vary depending upon the nature of the hybridization method and the composition and length of the hybridizing nucleic acid sequences. Generally, the temperature of hybridization and the ionic strength (such as the Na concentration) of the hybridization buffer will determine the stringency of hybridization. Calculations regarding hybridization conditions for attaining particular degrees of stringency are discussed in Sambrook et al., (1989) Molecular Cloning, second edition, Cold Spring Harbor Laboratory, Plainview, N.Y. (chapters 9 and 11).

As used herein, the term "detectable label" refers to any label that provides, directly or indirectly, a detectable signal, In some embodiments, a detectable label comprises a biological or chemical molecule, for example, enzymes, radio labeled molecules, fluorescent molecules or moieties, fluorophores, particles, chemiluminesors, enzyme substrates or cofactors, enzyme inhibitors, biotin, or magnetic particles. In other embodiments, a detectable label comprises a physical property, e.g., size, shape, electrophoretic mobility, hydrophobicity, hydrophilicity, solubility, and/or chromatographic behavior. In other embodiments, a detectable label comprises an identifier, e.g., a barcode.

As used herein, the term "fluorescent moiety" or "fluorescent molecules" refers to any compound that emits detectable fluorescence. Examples of fluorescent moieties are well known in the art and include, but are not limited to, coumarins and related dyes, tandem dyes, xanthene dyes (e.g., fluoresceins, rhodols and rhodamines), resorufins, cyanine dyes, bimanes, acridines, isoindoles, dansyl dyes, aminophthalic hydrazides (e.g., luminol and isoluminol derivatives), aminophthalimides, aminobenzofurans, aminoquinolines, dicyanohydroquinones, fluorescent europium, terbium complexes and related compounds. Exemplary fluorescent moieties include FITC, ROX, GFP, Cy5, Cy5.5, Cy3, Cy3B, GFP, YFP, RFP, CFP, Rhodamine Red, Texas Red, Bodipy, IDR700, LightCycler 610, LightCycler 640, LightCycler 670, LightCycler 705, and TAMRA.

"Real-time PCR" is a method for detecting and measuring products generated during each cycle of a PCR, which are proportionate to the amount of template nucleic acid prior to the start of PCR. The information obtained, such as an amplification curve, can be used to determine the presence of a target nucleic acid (such as *Mycoplasma* and related *Mollicutes* genus nucleic acids) and/or quantitate the initial amounts of a target nucleic acid sequence. Exemplary procedures for real-time PCR can be found in "Quantitation of DNA/RNA Using Real-Time PCR Detection" published by Perkin Elmer Applied Biosystems (1999) and to PCR Protocols (Academic Press New York, 1989).

In accordance with the present invention, there may be employed conventional molecular biology, microbiology, recombinant DNA, immunology, cell biology and other related techniques within the skill of the art. See, e.g., Sambrook et al., (2001) Molecular Cloning: A Laboratory Manual. 3$^{rd}$ ed. Cold Spring Harbor Laboratory Press: Cold Spring Harbor, N.Y.; Sambrook et al., (1989) Molecular Cloning: A Laboratory Manual. 2" ed. Cold Spring Harbor Laboratory Press: Cold Spring Harbor, N.Y.; Ausubel et al., eds. (2005) Current Protocols in Molecular Biology. John Wiley and Sons, Inc.: Hoboken, N.J.; Bonifacino et al., eds. (2005) Current Protocols in Cell Biology. John Wiley and Sons, Inc.: Hoboken, N.J.; Coligan et al., eds. (2005) Current Protocols in Immunology, John Wiley and Sons, Inc.: Hoboken, N.J.; Coico et al., eds. (2005) Current Protocols in Microbiology, John Wiley and Sons, Inc.: Hoboken, N.J.; Coligan et al., eds. (2005) Current Protocols in Protein Science, John Wiley and Sons, Inc.: Hoboken, N.J.; Enna et al., eds. (2005) Current Protocols in Pharmacology John Wiley and Sons, Inc.: Hoboken, N.J.; Hames et al., eds. (1999) Protein Expression: A Practical Approach. Oxford University Press: Oxford; Freshney (2000) Culture of Animal Cells: A Manual of Basic Technique. 4$^{th}$ ed. Wiley-Liss; among others. The Current Protocols listed above are updated several times every year.

*Mycoplasma* and Related *Mollicutes* Genus Nucleic Acid Sequences

In general, this invention relates to compositions, methods and kits to detect *Mycoplasma* and related *Mollicutes* genus which have contaminated a biological sample, such as for example, cell cultures in a laboratory setting, diagnostics and the like. The compositions comprise primers (used interchangeably herein with the term "oligonucleotides" or "oligomers") used in embodiments of the methods and kits and include one or more primers or oligonucleotides, each being complementary or substantially complementary to a portion of a 16S-23 S ribosomal RNA of a *Mycoplasma* and related *Mollicutes* genus. In one embodiment, two or more different oligonucleotides are contacted with the sample. In another embodiment, two or more different oligonucleotides are contacted with the sample and two or more different second oligonucleotides are contacted with the sample. In this embodiment, each oligonucleotide will be substantially complementary to a portion of the 16S-23S ribosomal RNA of a *Mycoplasma* species. For example, one oligonucleotide may be substantially complementary with approximately 90% of the nucleotides of the sequence pairing with the RNA of one species of *Mycoplasma* present in the sample but may only be substantially complementary with approximately 75% of the nucleotides of the sequence pairing with the RNA of another species of *Mycoplasma* present in the sample. However, the presence of both *Mycoplasma* species will be detected using the method of the assay. In one aspect of the invention, each of the oligonucleotides will be substantially complementary with greater than 90% of the nucleotides of the sequence pairing with a portion of the 16S-23S ribosomal RNA of each of the *Mycoplasma* species.

In preferred embodiments, the oligomers or primers for detecting *Mycoplasma* and related *Mollicutes* genus hybridize to the 16S-23S ribosomal RNA intergenic regions of *Mycoplasma* and related *Mollicutes* genus. In embodiments, the primers are complementary to at least about 5 consecutive nucleobases of the 16S-23S ribosomal RNA intergenic regions of *Mycoplasma* and related *Mollicutes* genus. In another embodiment, the primers are at least 60% complementary to at least about 5 consecutive nucleobases of the 16S-23S ribosomal RNA intergenic regions of *Mycoplasma* and related *Mollicutes* genus. In another preferred embodiment, the primers are at least 70% complementary to at least about 5 consecutive nucleobases of the 16S-23S ribosomal RNA intergenic regions of *Mycoplasma* and related *Mollicutes* genus. In another preferred embodiment, the primers are at least 80% complementary to at least about 5 consecutive nucleobases of the 16S-23S ribosomal RNA intergenic regions of *Mycoplasma* and related *Mollicutes* genus. In another preferred embodiment, the primers are at least 90% complementary to at least about 5 consecutive nucleobases of the 16S-23S ribosomal RNA intergenic regions of *Mycoplasma* and related *Mollicutes* genus. In another preferred embodiment, the primers are at least 95%, 96%, 97%, 98%, 99% complementary to at least about 5 consecutive nucleobases in either the 5' to 3' or 3' to 5' directions of the 16S-23S ribosomal RNA intergenic regions of *Mycoplasma* and related *Mollicutes* genus.

In one embodiment, an isolated or synthetic nucleic acid which hybridizes to at least 5 consecutive nucleic acids in a 5' to 3' or 3' to 5' direction of a 16S-23S ribosomal intergenic region nucleic acid of *Mycoplasma* and/or related *Mollicutes* genus strains. In some embodiments, the isolated or synthetic nucleic acid comprises at least five nucleic acids. The isolated or synthetic nucleic acid optionally comprises one or more mutations, variants, substitutions, analogs, deletions or combinations thereof. Examples, of such mutations, variants, substitutions, analogs, comprise: adenine, guanine, thymine, cytosine, uracil, purine, xanthine, diaminopurine, 8-oxo-$N^6$-methyladenine, 7-deazaxanthine, 7-deazaguanine, $N^4,N^4$-ethanocytosin, $N^6,N^6$-ethano-2,6-diaminopurine, 5-methylcytosine, 5-($C^3$-$C^6$)-alkynylcytosine, 5-fluorouracil, 5-bromouracil, pseudoisocytosine, 2-hydroxy-5-methyl-4-triazolopyridin, isocytosine, isoguanin, inosine, non-naturally occurring nucleobases, locked nucleic acids (LNA), or peptide nucleic acids (PNA). In embodiments, the isolated or synthetic nucleic acid hybridizes to *Mycoplasma* and/or related *Mollicutes* genus strains, comprising: *Acholeplasma laidlawii* ATCC23206; *Spiroplasma citri* ATCC27556; *M. arginini* ATCC23838; *M. arthritidis* ATCC19611; *M. Bovis* ATCC25025; *M. capricolum capricolum* ATCC27343; *M. fermentans* ATCC49892; *M. gallisepticum* ATCC19610; *M. genitalium* ATCC33530; *M. hominis* ATCC27545; *M. hyopneumoniae* ATCC25934; *M. orale* ATCC23714; *M. pirum* ATCC25960; *M. pneumoniae* ATCC15531; *M. pulmonis* GenBank X58554; *M. salivarium* ATCC23064; *M. synoviae* ATCC25204; *M. mirounga* GenBank GU905026; *M. adleri* strain G145; *M. agalactiae* strainGO-5; *M. agassizii* strain PS6; *M. alkalescens* ATCC29103; *M. alligatoris* ATCC700619; *M. alvi* strain Ilsley; *M. amphoriforme* strain A39; *M. anseris* strain 1219; *M. auris* strain UTA; *M. bovigenitalium* strain PG-11; *M. bovirhinis* ATCC27748; *M. bovoculi* ATCC29104; *M. buccale* ATCC23636; *M. buteonis* strain Bb/T2g; *M. californicum* strain ST6; *M. canadense* strain 466; *M. canimucosale* type strain 1642; *M. canis* ATCC19525; *M. caviae* strain ATCC27108; *M. cavipharyngis* ATCC43016; *M. citelli* strain RG2C; *M. cloacale* strain 383; *M. collis* ATCC35278; *M. columbinasale* ATCC33549; *M. columbinum* strain FG295; *M. columborale* ATCC29258; *M. conjunctivae* Goat655; *M. corogypsi* strain BV1-5; *M. cottewii* ATCC43093; *M. cricetuli* ATCC35279; *M. crocodyli* ATCC51981; *M. cynos* strain H381; *M. dispar* ATCC27140; *M. edwardii* strain 04-3440; *M. elephantis* ATCC51980; *M. equigenitalium* ATCC29869; *M. equirhinis* ATCC29420; *M. falconis* ATCC51372; *M. fastidiosum* ATCC33229; *M. faucium* ATCC25293; *M. feliminutum* ATCC25749; *M. felis* GenBank AF443608; *M. flocculare* strain Ms42; *M. gallinarum* strain B2Dinter; *M. gallisepticum* GenBank FJ468427; *M. gallopavonis* ATCC33551; *M. glycophilum* ATCC35277; *M. gypis* ATCC51370; *M. hyopharyngis* strain H36B-F; *M. hyorhinis* ATCC29052; *M. iguanae* strain 2327; *M. indiense* ATCC51125; *M. iners* ATCC15969; *M. iowae* ATCC33552;

*M. lagogenitalium* ATCC700289; *M. leachii* strain PG50; *M. leonicaptivi* ATCC49890; *M. leopharyngis* ATCC49889; *M. lipofaciens* ATCC35015; *M. lipophilum* ATCC27104; *M. maculosum* strain PG15; *M. meleagridis* ATCC27764; *M. microti* strain IL371; *M. moatsii* strain MK405; *M. mobile* ATCC43663; *M. molare* strain H542; *M. muris* ATCC33757; *M. mustelae* ATCC35214; *M. neurolyticum* ATCC19988; *M. opalescens* strain MHS408; *M. ovipneumoniae* ATCC29419; *M. oxoniensis* ATCC49694; *M. phocicerebrale* strain CSL5195S2; *M. phocirhinis* strain CSL7475-4; *M. primatum* strain HRC292; *M. pullorum* ATCC33553; *M. putrefaciens* ATCC33756; *M. simbae* ATCC49888; *M. spermatophilum* strain AH159; *M. sphenisci* strain UCMJ; *M. spumans* ATCC19526; *M. sturni* ATCC51945; *M. sualvi* ATCC33004; *M. subdolum* ATCC29870; *M. testudineum* ATCC700618; *M. testudinis* ATCC43263; *M. verecundum* ATCC27862; *M. vulturii* strain Gb-V33; *M. yeatsii* ATCC43094; *M. zalophi* strain CSL5195; or *M. zalophidermidis* strain CSL4779.

In preferred embodiments, the isolated or synthetic nucleic acid o hybridizes to the 16S-23S ribosomal intergenic region of *Mycoplasma* and related *Mollicutes* genus strains, under low-, medium- or high stringency conditions. The conditions used in the methods are described in detail in the Examples which follow.

While the specific sequences of certain exemplary target segments are set forth herein, one of skill in the art will recognize that these serve to illustrate and describe particular embodiments within the scope of the present invention. Additional target segments are readily identifiable by one having ordinary skill in the art in view of this disclosure.

Target segments 5-100 nucleobases in length comprising a stretch of at least five (5) consecutive nucleobases selected from within the illustrative preferred target segments are considered to be suitable for targeting as well.

Sequence identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Homologs or orthologs of nucleic acid or amino acid sequences possess a relatively high degree of sequence identity/similarity when aligned using standard methods.

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene*, 73:237-44, 1988; Higgins & Sharp, CABIOS 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI, National Library of Medicine, Bethesda, Md. 20894) and on the Internet, for use in connection with the sequence analysis programs blastp, blastn, blastx, tblastn, and tblastx. Blastn is used to compare nucleic acid sequences, while blastp is used to compare amino acid sequences. Additional information can be found at the NCBI web site.

Once aligned, the number of matches is determined by counting the number of positions where an identical nucleotide or amino acid residue is present in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a nucleic acid sequence that has 1166 matches when aligned with a test sequence having 1554 nucleotides is 75.0 percent identical to the test sequence (1166/1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer. In another example, a target sequence containing a 20-nucleotide region that aligns with 20 consecutive nucleotides from an identified sequence contains a region that shares 75 percent sequence identity to that identified sequence (i.e., 15/20*100=75).

One indication that two nucleic acid molecules are closely related is that the two molecules hybridize to each other under stringent conditions. Stringent conditions are sequence-dependent and are different under different environmental parameters.

The nucleic acid oligomers or primers disclosed herein are not limited to the exact sequences shown, as those skilled in the art will appreciate that changes can be made to a sequence, and not substantially affect the ability of the primer to function as desired. For example, sequences having at least 80%, at least 90%, at least 95%, at least 96%, at least 97%, at least 98%, or at least 99%, such as 100% sequence identity to any of SEQ ID NOS: 1 to 15 are provided herein. One of skill in the art will appreciate that these sequence identity ranges are provided for guidance only; it is possible that primers can be used that fall outside these ranges.

In general embodiments, the sequence identity or complementarity, between a primer or oligonucleotide in either the 5' to 3' or 3' to 5' directions of the 16S-23S ribosomal RNA intergenic regions of *Mycoplasma* and related *Mollicutes* genus target sequences is from about 50% to about 60%. In some embodiments, sequence identity or complementarity, is from about 60% to about 70%. In some embodiments, sequence identity or complementarity, is from about 70% to about 80%. In some embodiments, sequence identity or complementarity, is from about 80% to about 90%. In some embodiments, sequence identity or complementarity, is about 90%, about 92%, about 94%, about 95%, about 96%, about 97%, about 98%, about 99% or about 100%. The length of the primer is generally 7-mer to 100-mer, preferably 15-mer to 40-mer, preferably 18-mer to 30-mer. The number of nucleotides to be substituted, added or deleted is not particularly limited and varies depending on the length of the primer or the like. For example, 1 to 5, or 1 to 3, or 1 to 2, or 1. The identity of a nucleotide sequence can be determined as described in detail in the Examples section which follows, using bioinformatics analysis.

In further embodiments, the primers or oligonucleotides of the present invention are not particularly limited with respect to their sequences, as long as each primer has a nucleotide sequence that satisfies the general embodiments, and may be any primer such as a DNA primer, an RNA primer, or a primer using a DNA or RNA analog.

In some embodiments, the isolated nucleic acid comprises a sequence identity of at least about 50% to about 99.99% to a portion of the 16S-23S ribosomal RNA intergenic regions of *Mycoplasma* and related *Mollicutes* genus of either the 5' to 3' or 3' to 5' direction or sense and anti-sense orientation.

In further embodiments, the primers or oligonucleotides of the present invention are not particularly limited with respect to their sequences, as long as each primer has a nucleotide sequence that satisfies the general embodiments, and may be any primer such as a DNA primer, an RNA primer, or a primer using a DNA or RNA analog. In preferred embodiments, the primers or oligonucleotides comprise SEQ ID NOS: 1 to 15, mutants, variants, analogs or fragments thereof.

In other preferred embodiments, the oligomers, primers or oligonucleotides set forth in SEQ ID NOS: 1 to 15, comprise one or more mutations, deletions, additions or substitutions. In other embodiments, the primer can be composed of a nucleotide sequence with an identity of 60% or more, preferably 70% or more, more preferably 88% or more to the nucleotide sequence of any of the above-mentioned primers set forth as SEQ ID NOS: 1-15 in either the sense or anti-sense orientation. Annealing conditions and the PCR cycle steps are not particularly limited and can be appropriately selected by a person skilled in the art.

In other preferred embodiments, the primers or oligonucleotides comprise one or more mutations, deletions, additions or substitutions. In other embodiments, the primer can be composed of a nucleotide sequence with an identity of about 50% or more, preferably 70% or more, more preferably 88% or more to the nucleotide sequence of any of the above-mentioned primers in either the sense or anti-sense orientation. Annealing conditions and the PCR cycle steps are not particularly limited and can be appropriately selected by a person skilled in the art.

In a preferred embodiment, the primers or oligomers comprise one or more substituted nucleic acid bases. In other embodiments, the oligomers, primers or oligonucleotides comprise one or more deletions, insertions, substitutions or combinations thereof. Examples of insertions and substitutions, include without limitation: adenine, guanine, thymine, cytosine, uracil, purine, xanthine, diaminopurine, 8-oxo-$N^6$-methyladenine, 7-deazaxanthine, 7-deazaguanine, $N^4,N^4$-ethanocytosin, $N^6,N^6$-ethano-2,6-diaminopurine, 5-methylcytosine, 5-($C^3$-$C^6$)-alkynylcytosine, 5-fluorouracil, 5-bromouracil, pseudoisocytosine, 2-hydroxy-5-methyl-4-triazolopyridin, isocytosine, isoguanin, inosine, non-naturally occurring nucleobases, locked nucleic acids (LNA), or peptide nucleic acids (PNA).

In another preferred embodiment, the primers or oligomers of the present invention also include variants in which a different base is present at one or more of the nucleotide positions in the compound. For example, if the first nucleotide is an adenosine, variants may be produced which contain thymidine, guanosine or cytidine at this position. However, it may also be an analog such as bromodeoxyuridine. These compounds are then tested using the methods described herein to determine their ability to detect *Mycoplasma*.

In another preferred embodiment, a primer or oligonucleotide comprises combinations of phosphorothioate internucleotide linkages and at least one internucleotide linkage selected from the group consisting of: alkylphosphonate, phosphorodithioate, alkylphosphonothioate, phosphoramidate, carbamate, carbonate, phosphate triester, acetamidate, carboxymethyl ester, and/or combinations thereof.

In another preferred embodiment, a primer or oligonucleotide optionally comprises at least one modified nucleobase comprising, peptide nucleic acids, locked nucleic acid (LNA) molecules, analogues, derivatives and/or combinations thereof.

In some embodiments, an oligonucleotide is labeled with a detectable moiety. The detectable moiety may be a chemical label such as an enzyme, a fluorescent compound, a radioisotope, a chromophore, a luminescent compound or any detectable moiety.

Probes:

In other embodiments, the primers or oligomers embodied herein can also be utilized as probes. Thus, for example, the probes for detecting *Mycoplasma* and related *Mollicutes* genus hybridize to the 16S-23S ribosomal RNA intergenic regions of *Mycoplasma* and related *Mollicutes* genus. In embodiments, the probes are complementary to at least about 5 consecutive nucleobases of the 16S-23S ribosomal RNA intergenic regions of *Mycoplasma* and related *Mollicutes* genus. In another embodiment, the probes are at least 60% complementary to at least about 5 consecutive nucleobases of the 16S-23S ribosomal RNA intergenic regions of *Mycoplasma* and related *Mollicutes* genus. In another preferred embodiment, the probes are at least 70% complementary to at least about 5 consecutive nucleobases of the 16S-23S ribosomal RNA intergenic regions of *Mycoplasma* and related *Mollicutes* genus. In another preferred embodiment, the probes are at least 80% complementary to at least about 5 consecutive nucleobases of the 16S-23S ribosomal RNA intergenic regions of *Mycoplasma* and related *Mollicutes* genus. In another preferred embodiment, the probes are at least 90% complementary to at least about 5 consecutive nucleobases of the 16S-23S ribosomal RNA intergenic regions of *Mycoplasma* and related *Mollicutes* genus. In another preferred embodiment, the probes are at least 95%, 96%, 97%, 98%, 99% complementary to at least about 5 consecutive nucleobases in either the 5' to 3' or 3' to 5' directions of the 16S-23S ribosomal RNA intergenic regions of *Mycoplasma* and related *Mollicutes* genus.

Probes are generally at least 20 nucleotides in length, such as at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50 at least 51, at least 52, at least 53, at least 54, at least 55, at least 56, at least 57, at least 58, at least 59, at least 60, or more contiguous nucleotides complementary to the target nucleic acid molecule, such as 20-60 nucleotides, 30-60 nucleotides, 20-50 nucleotides, 30-50 nucleotides, 20-40 nucleotides, or 20-30 nucleotides.

In some embodiments, the probe is detectably labeled, either with an isotopic or non-isotopic label. Non-isotopic labels can include a fluorescent or luminescent molecule, biotin, an enzyme or enzyme substrate or a chemical. Such labels are preferentially chosen such that the hybridization of the probe with target nucleic acid (such as a *Mycoplasma* and related *Mollicutes* genus strains, for example, the 16S-23S ribosomal RNA intergenic regions of *Mycoplasma* and related *Mollicutes* genus molecules, or subsequence thereof) can be detected. In some examples, the probe is labeled with a fluorophore. Examples of suitable fluorophore labels are given above. In some examples, the fluorophore is a donor fluorophore. In other examples, the fluorophore is an accepter fluorophore, such as a fluorescence quencher. In some examples, the probe includes both a donor fluorophore and an accepter fluorophore, for example a donor fluorophore such as a FAM and an acceptor fluorophore such as a BLACK HOLE™ quencher. Appropriate donor/acceptor fluorophore pairs can be selected using routine methods. In one example, the donor emission wavelength is one that can significantly excite the acceptor, thereby generating a detectable emission from the acceptor. In some examples, the probe is modified at the 3'-end to prevent extension of the probe by a polymerase.

In particular examples, the acceptor fluorophore (such as a fluorescence quencher) is attached to the 3' end of the probe and the donor fluorophore is attached to a 5' end of the probe. In other examples, the acceptor fluorophore (such as a fluorescence quencher) is attached to the 5' end of the probe and the donor fluorophore is attached to a 3' end of the probe. In another particular example, the acceptor fluorophore (such as a fluorescence quencher) is attached to a modified nucleotide (such as a T) and the donor fluorophore is attached to a 5' end of the probe. Methods for labeling and guidance in the choice of labels appropriate for various purposes are discussed, for example, in Sambrook et al., Molecular Cloning: A Laboratory Manual, Cold Spring Harbor Laboratory Press (1989) and Ausubel et al., Current Protocols in Molecular Biology, Greene Publishing Associates and Wiley-Intersciences (1987). In a particular example, a probe includes at least one detectable label, for example, a fluorophore, such as an acceptor fluorophore or donor fluorophore. For example, a fluorophore can be attached at the 5'- or 3'-end of the probe. In specific examples, the fluorophore is attached to the base at the 5'-end of the probe, the base at its 3'-end, the phosphate group at its 5'-end or a modified base, such as a T internal to the probe.

Detection of *Mycoplasma* and Related *Mollicutes* Genus

Besides the application for the detection of *Mycoplasma* and related *Mollicutes* genus strains in tissue or cell cultures, other applications of the *Mycoplasma* and related *Mollicutes* genus strain specific primers and probes disclosed herein, is for the detection of *Mycoplasma* and related *Mollicutes* genus strains in a sample, such as a biological sample obtained from a subject that has or is suspected of having a *Mycoplasma* and/or related *Mollicutes* genus strains, infection, for example, *M. pneumoniae* which causes primary atypical pneumonia in humans. Thus, the disclosed methods can be used to diagnose if a subject is infected by *Mycoplasma* and related *Mollicutes* genus strains. Accordingly, methods for the detection of *Mycoplasma* or related *Mollicutes* genus strain nucleic acids are disclosed. Non-limiting examples of *Mycoplasma* and related *Mollicutes* genus strains comprise: *Acholeplasma laidlawii* ATCC23206; *Spiroplasma citri* ATCC27556; *M. arginini* ATCC23838; *M. arthritidis* ATCC19611; *M. bovis* ATCC25025; *M. capricolum capricolum* ATCC27343; *M. fermentans* ATCC49892; *M. gallisepticum* ATCC19610; *M. genitalium* ATCC33530; *M. hominis* ATCC27545; *M. hyopneumoniae* ATCC25934; *M. orate* ATCC23714; *M. pirum* ATCC25960; *M. pneumoniae* ATCC15531; *M. pulmonis* GenBank X58554; *M. salivarium* ATCC23064; *M. synoviae* ATCC25204; *M. mirounga* GenBank GU905026; *M. adleri* strain G145; *M. agalactiae* strainGO-5; *M. agassizii* strain PS6; *M. alkalescens* ATCC29103; *M. alligatoris* ATCC700619; *M. alvi* strain Ilsley; *M. amphoriforme* strain A39; *M. anseris* strain 1219; *M. auris* strain UTA; *M. bovigenitalium* strain PG-11; *M. bovirhinis* ATCC27748; *M. bovoculi* ATCC29104; *M. buccale* ATCC23636; *M. buteonis* strain Bb/T2g; *M. californicum* strain ST6; *M. canadense* strain 466; *M. canimucosale* type strain 1642; *M. canis* ATCC19525; *M. caviae* strain ATCC27108; *M. cavipharyngis* ATCC43016; *M. citelli* strain RG2C; *M. cloacale* strain 383; *M. collis* ATCC35278; *M. columbinasale* ATCC33549; *M. columbinum* strain FG295; *M. columborale* ATCC29258; *M. conjunctivae* Goat655; *M. corogypsi* strain BV1-5; *M. cottewii* ATCC43093; *M. cricetuli* ATCC35279; *M. crocodyli* ATCC51981; *M. cynos* strain H381; *M. dispar* ATCC27140; *M. edwardii* strain 04-3440; *M. elephantis* ATCC51980; *M. equigenitalium* ATCC29869; *M. equirhinis* ATCC29420; *M. falconis* ATCC51372; *M. fastidiosum* ATCC33229; *M. faucium* ATCC25293; *M. feliminutum* ATCC25749; *M. felis* GenBank AF443608; *M. flocculare* strain Ms42; *M. gallinarum* strain B2Dinter; *M. gallisepticum* GenBank FJ468427; *M. gallopavonis* ATCC33551; *M. glycophilum* ATCC35277; *M. gypis* ATCC51370; *M. hyopharyngis* strain H36B-F; *M. hyorhinis* ATCC29052; *M. iguanae* strain 2327; *M. indiense* ATCC51125; *M. iners* ATCC15969; *M. iowae* ATCC33552; *M. lagogenitalium* ATCC700289; *M. leachii* strain PG50; *M. leonicaptivi* ATCC49890; *M. leopharyngis* ATCC49889; *M. lipofaciens* ATCC35015; *M. lipophilum* ATCC27104; *M. maculosum* strain PG15; *M. meleagridis* ATCC27764; *M. microti* strain IL371; *M. moatsii* strain MK405; *M. mobile* ATCC43663; *M. molare* strain H542; *M. muris* ATCC33757; *M. mustelae* ATCC35214; *M. neurolyticum* ATCC19988; *M. opalescens* strain MHS408; *M. ovipneumoniae* ATCC29419; *M. oxoniensis* ATCC49694; *M. phocicerebrale* strain CSL5195S2; *M. phocirhinis* strain CSL7475-4; *M. primatum* strain HRC292; *M. pullorum* ATCC33553; *M. putrefaciens* ATCC33756; *M. simbae* ATCC49888; *M. spermatophilum* strain AH159; *M. sphenisci* strain UCMJ; *M. spumans* ATCC19526; *M. sturni* ATCC51945; *M. sualvi* ATCC33004; *M. subdolum* ATCC29870; *M. testudineum* ATCC700618; *M. testudinis* ATCC43263; *M. verecundum* ATCC27862; *M. vulturii* strain Gb-V33; *M. yeatsii* ATCC43094; *M. zalophi* strain CSL5195; or *M. zalophidermidis* strain CSL4779.

In embodiments, a method of detecting *Mycoplasma* and/or related *Mollicutes* genus strains comprises contacting a sample with one or more primers set forth as SEQ ID NOS: 1 to 15 mutants, variants, analogs or fragments thereof. In preferred embodiments, a method of detecting *Mycoplasma* and related *Mollicutes* genus strains comprises contacting a sample with at least two primers set forth as SEQ ID NOS: 1 to 15, mutants, variants, analogs or fragments thereof. In other embodiments, the oligomers, primers or oligonucleotides set forth in SEQ ID NOS: 1 to 15, comprise one or more mutations, deletions, additions or substitutions. In other embodiments, the primer can be composed of a nucleotide sequence with an identity of 60% or more, preferably 70% or more, more preferably 88% or more to the nucleotide sequence of any of the above-mentioned primers set forth as SEQ ID NOS: 1-15 in either the sense or anti-sense orientation. Annealing conditions and the PCR cycle steps are not particularly limited and can be appropriately selected by a person skilled in the art.

The methods described herein may be used for any purpose for which detection of *Mycoplasma* and related *Mollicutes* genus strains is desirable, including diagnostic and prognostic applications, such as in laboratory and clinical settings. Appropriate samples include any conventional environmental or biological samples, including clinical samples obtained from a human or veterinary subject. Suitable samples include all biological samples useful for detection of bacterial infection in subjects, including, but not limited to, cells, tissues (for example, lung, liver and kidney), bone marrow aspirates, bodily fluids (for example, blood, serum, urine, cerebrospinal fluid, bronchoalveolar lavage, tracheal aspirates, sputum, nasopharyngeal aspirates, oropharyngeal aspirates, saliva), eye swabs, cervical swabs, vaginal swabs, rectal swabs, stool, and stool suspensions. Other suitable samples include samples obtained from middle ear fluids, bronchoalveolar levage, tracheal aspirates, sputum, nasopharyngeal aspirates, oropharyngeal aspirates, or saliva. Standard techniques for acquisition of such samples are available. See for example, Schluger et al., *J. Exp. Med.* 176:1327-33 (1992); Bigby et al., *Am. Rev. Respir. Dis.* 133:515-18 (1986); Kovacs et al., *NEJM* 318: 589-93 (1988); and Ognibene et al., *Am. Rev. Respir. Dis.* 129:929-32 (1984).

Detecting a *Mycoplasma* or related *Mollicutes* genus strain nucleic acids in a sample involves contacting the sample with at least one of the probes embodied herein that is capable of hybridizing to a *Mycoplasma* or related *Mollicutes* genus strains, such as the 16S-23S ribosomal RNA intergenic regions of *Mycoplasma* or related *Mollicutes* genus molecules, or subsequence thereof, under conditions of low to high stringency, and detecting hybridization between the 16S-23S ribosomal RNA intergenic regions of *Mycoplasma* or related *Mollicutes* genus molecules, or subsequence thereof, and the probe. Detection of hybridization between the probe and the *Mycoplasma* or related *Mollicutes* genus strain nucleic acid indicates the presence of a *Mycoplasma* or *Mollicutes* nucleic acid or organism in the sample, for example detection of hybridization between the probes embodied herein, and *M. pneumoniae* nucleic acid indicates the presence of the *M. pneumoniae* nucleic acid in the sample.

In some embodiments, *Mycoplasma* or related *Mollicutes* genus strain nucleic acids present in a sample are amplified prior to using a hybridization probe for detection. For instance, it can be advantageous to amplify a portion of the *Mycoplasma* or related *Mollicutes* genus strain nucleic acid, and then detect the presence of the amplified nucleic acid. For example, to increase the number of nucleic acids that can be detected, thereby increasing the signal obtained. *Mycoplasma* or related *Mollicutes* genus strain specific nucleic acid primers can be used to amplify a region that is at least about 50, at least about 60, at least about 70, at least about 80 at least about 90, at least about 100, at least about 200, or more base pairs in length to produce amplified *Mycoplasma* or related *Mollicutes* genus strain specific nucleic acids. In preferred embodiments, the amplification is conducted by real time PCR.

Detecting the amplified product typically includes the use of labeled probes that are sufficiently complementary and hybridize to the amplified *Mycoplasma* or related *Mollicutes* genus strain nucleic acid sequence. Thus, the presence, amount, and/or identity of the amplified product can be detected by hybridizing a labeled probe, such as a fluorescently labeled probe, complementary to the amplified product.

Preferred methods for detecting *Mycoplasma* or related *Mollicutes* genus strains are described in detail, in the Examples section which follow. In one embodiment, the *Mycoplasma* or related *Mollicutes* genus strains are detected by amplification using real time PCR. However, other methods or combinations of methods are also embodied herein. In one embodiment, the detection of a target nucleic acid sequence of interest, includes the combined use of PCR amplification and a labeled probe such that the product is measured using real-time PCR. In another embodiment, the detection of an amplified target nucleic acid sequence of interest includes the transfer of the amplified target nucleic acid to a solid support, such as a blot, for example, a Northern blot, and probing the blot with a probe, for example a labeled probe, that is complementary to the amplified target nucleic acid sequence. In yet another embodiment, the detection of an amplified target nucleic acid sequence of interest includes the hybridization of a labeled amplified target nucleic acid to probes disclosed herein that are arrayed in a predetermined array with an addressable location and that are complementary to the amplified target nucleic acid.

Any nucleic acid amplification method can be used to detect the presence of *Mycoplasma* or related *Mollicutes* genus strain nucleic acid in a sample. In one specific, non-limiting example, polymerase chain reaction (PCR) is used to amplify the *Mycoplasma* or related *Mollicutes* genus strain nucleic acid sequences. In other specific, non-limiting examples, real-time PCR, reverse transcriptase-polymerase chain reaction (RT-PCR), real-time reverse transcriptase-polymerase chain reaction (RT-PCR), ligase chain reaction, or transcription-mediated amplification (TMA) is used to amplify the *Mycoplasma* or related *Mollicutes* genus strain nucleic acid. Techniques for nucleic acid amplification are well-known to those of skill in the art.

Typically, at least two primers are utilized in the amplification reaction. Amplification of the *Mycoplasma* or related *Mollicutes* genus strain nucleic acid involves contacting the *Mycoplasma* or related *Mollicutes* genus strain nucleic acid with one or more primers that are capable of hybridizing to and directing the amplification of a *Mycoplasma* or related *Mollicutes* genus strain nucleic acid, such as a primer capable of hybridizing under low to high stringency conditions to a *Mycoplasma* or related *Mollicutes* genus strain nucleic acid sequence, for example a primer that is least 50% identical to the nucleotide sequence set forth as one of SEQ ID NOS: 1 to 15.

In some embodiments, the sample is contacted with a pair of primers that include a forward and reverse primer that both hybridize to a *Mycoplasma* or related *Mollicutes* genus strain nucleic acid, such as a primer that is least 50% identical to the nucleotide sequence set forth as SEQ ID NOS: 1 to 15.

In other embodiments, the sample is contacted with at least two primers, that includes one or more primers set forth as SEQ ID NOS: 1 to 9 and SEQ ID NOS: 10-15. In other embodiments, the sample is contacted with at least two primers, that includes one or more primers set forth as SEQ ID NOS: 1 to 9, SEQ ID NOS: 10-15 or combinations thereof.

The amplified *Mycoplasma* or related *Mollicutes* genus strain nucleic acid, can be detected in real-time, for example by real-time PCR, in order to determine the presence, and/or the amount of *Mycoplasma* or related *Mollicutes* genus strain nucleic acid specific nucleic acid in a sample. In this manner an amplified nucleic acid sequence, such as an amplified *Mycoplasma* or related *Mollicutes* genus strain nucleic acid sequence, can be detected using a probe specific for the product amplified from the *Mycoplasma* or related *Mollicutes* genus strain nucleic acid sequence of interest, such as an amplified *Mycoplasma* nucleic acid sequence.

Real-time PCR monitors the fluorescence emitted during the reaction as an indicator of amplicon production during each PCR cycle as opposed to the endpoint detection. The real-time progress of the reaction can be viewed in some systems. Typically, real-time PCR uses the detection of a fluorescent reporter. Typically, the fluorescent reporter's signal increases in direct proportion to the amount of PCR product in a reaction. By recording the amount of fluorescence emission at each cycle, it is possible to monitor the PCR reaction during exponential phase where the first significant increase in the amount of PCR product correlates to the initial amount of target template. The higher the starting copy number of the nucleic acid target, the sooner a significant increase in fluorescence is observed.

In one embodiment, the fluorescently-labeled probes rely upon fluorescence resonance energy transfer (FRET), or in a change in the fluorescence emission wavelength of a sample, as a method to detect hybridization of a DNA probe to the amplified target nucleic acid in real-time. For example, FRET that occurs between fluorogenic labels on different probes (for example, using HybProbes) or between a fluorophore and a non-fluorescent quencher on the same probe (for example, using a molecular beacon or a TAQMAN™ probe) can identify a probe that specifically hybridizes to the DNA sequence of interest and in this way, using a *Mycoplasma* or related *Mollicutes* genus strain nucleic acid probe, can detect the presence, and/or amount of a *Mycoplasma* or related *Mollicutes* genus strain nucleic acid in a sample. In some embodiments, the fluorescently-labeled DNA probes used to identify amplification products have spectrally distinct emission wavelengths, thus allowing them to be distinguished within the same reaction tube, for example in multiplex PCR, for example a multiplex real-time PCR. In some embodiments, the probes and primers disclosed herein are used in multiplex real-time PCR.

In another embodiment, a melting curve analysis of the amplified target nucleic acid can be performed subsequent to the amplification process. The $T_m$ of a nucleic acid sequence depends on the length of the sequence and its G/C content. Thus, the identification of the $T_m$ for a nucleic acid sequence can be used to identify the amplified nucleic acid, for example by using double-stranded DNA binding dye chemistry, which quantitates the amplicon production by the use of a non-sequence specific fluorescent intercalating agent (such as SYBR-green or ethidium bromide). SYBR green is a fluorogenic minor groove binding dye that exhibits little fluorescence when in solution but emits a strong fluorescent signal upon binding to double-stranded DNA. Typically, SYBR green is used in singleplex reactions, however when coupled with melting point analysis, it can be used for multiplex reactions.

Any type of thermal cycler apparatus can be used for the amplification of the *Mycoplasma* or related *Mollicutes* genus strain nucleic acid. Examples of suitable apparatuses include a PTC-100™ Peltier Thermal Cycler (MJ Research, Inc.; San Francisco, Calif.), a ROBOCYCLER™ 40 Temperature Cycler (Stratagene; La Jolla, Calif.), or a GENEAMP™ PCR System 9700 (Applied Biosystems; Foster City, Calif.). For real-time PCR, any type of real-time thermocycler apparatus can be used. For example, a BioRad iCycler iQ™ LIGHTCYCLER™ (Roche; Mannheim, Germany), a 7700 Sequence Detector (Perkin Elmer/Applied Biosystems; Foster City, Calif.), ABI™ systems such as the 7000, 7500, 7700, or 7900 systems (Applied Biosystems; Foster City, Calif.), or an MX4000™, MX3000™ or MX3005™ (Stratagene; La Jolla, Calif.); DNA Engine Opticon Continuous Fluorescence Detection System (MJ Research); and Cepheid SMARTCYCLER™ can be used to amplify nucleic acid sequences in real-time.

In some embodiments, detecting the presence of a *Mycoplasma* or related *Mollicutes* genus strain nucleic acid sequence in a sample includes the extraction of *Mycoplasma* or related *Mollicutes* genus strain DNA. DNA extraction relates to releasing DNA from a latent or inaccessible form in a cell or sample and allowing the DNA to become freely available. In such a state, it is suitable for effective detection and/or amplification of the *Mycoplasma* or related *Mollicutes* genus strain nucleic acid. Releasing DNA may include steps that achieve the disruption of cells. Additionally, extraction of DNA may include steps that achieve at least a partial separation of the DNA dissolved in an aqueous medium from other cellular components, wherein such components may be either particulate or dissolved.

In some embodiments, detecting the presence of a *Mycoplasma* or related *Mollicutes* genus strain nucleic acid sequence in a sample includes the extraction of *Mycoplasma* or related *Mollicutes* genus strain RNA. RNA extraction relates to releasing RNA from a latent or inaccessible form in a cell or sample and allowing the RNA to become freely available. In such a state, it is suitable for effective detection and/or amplification of the *Mycoplasma* or related *Mollicutes* genus strain nucleic acid. Releasing RNA may include steps that achieve the disruption of cells. Extraction of RNA is generally carried out under conditions that effectively exclude or inhibit any ribonuclease activity that may be present. Additionally, extraction of RNA may include steps that achieve at least a partial separation of the RNA dissolved in an aqueous medium from other cellular components, wherein such components may be either particulate or dissolved.

One of ordinary skill in the art will know suitable methods for extracting nucleic acids such as RNA and/or DNA from a sample; such methods will depend upon, for example, the type of sample in which the *Mycoplasma* or related *Mollicutes* genus strain nucleic acid is found. For example, the nucleic acids may be extracted using guanidinium isothiocyanate, such as the single-step isolation by acid guanidinium isothiocyanate-phenol-chloroform extraction of Chomczynski et al. (*Anal. Biochem.* 162:156-59, 1987). The sample can be used directly or can be processed, such as by adding solvents, preservatives, buffers, or other compounds or substances. Nucleic acids can be extracted using standard methods. For instance, rapid nucleic acid preparation can be performed using a commercially available kit (such as the QIAGEN™ DNA Mini kit (QIAGEN™) Roche MagNA Pure Compact Nucleic Acid Isolation Kit I or RNEASY™ Mini Kit (QIAGEN™); NUCLISENS™ NASBA Diagnostics (bioMerieux); or the MASTERPURE™ Complete DNA and RNA Purification Kit (EPICENTRE)).

In some embodiments, the probe is detectably labeled, either with an isotopic or non-isotopic label; in alternative embodiments, the *Mycoplasma* or related *Mollicutes* genus nucleic acid is labeled. Non-isotopic labels can, for instance, comprise a fluorescent or luminescent molecule, or an enzyme, co-factor, enzyme substrate, or hapten. The probe is incubated with a single-stranded or double-stranded preparation of RNA, DNA, or a mixture of both, and hybridization determined. In some examples, the hybridization results in a detectable change in signal such as in increase or decrease in signal, for example from the labeled probe. Thus, detecting hybridization comprises detecting a change in signal from the labeled probe during or after hybridization relative to signal from the label before hybridization.

Arrays:

An array containing a plurality of heterogeneous probes for the detection, of *Mycoplasma* or related *Mollicutes* genus strain nucleic acid are disclosed. Such arrays may be used to rapidly detect *Mycoplasma* or related *Mollicutes* genus strain nucleic acid in a sample.

Arrays are arrangements of addressable locations on a substrate, with each address containing a nucleic acid, such as a probe embodied herein. In some embodiments, each address corresponds to a single type or class of nucleic acid, such as a single probe, though a particular nucleic acid may be redundantly contained at multiple addresses. A "microarray" is a miniaturized array requiring microscopic examination for detection of hybridization. Larger "macroarrays" allow each address to be recognizable by the naked human eye and, in some embodiments, a hybridization signal is detectable without additional magnification. The addresses may be labeled, keyed to a separate guide, or otherwise identified by location.

In some embodiments, a *Mycoplasma* or related *Mollicutes* genus strain nucleic acid detection array is a collection of separate probes at the array addresses. The detection array is then contacted with a sample suspected of containing *Mycoplasma* or related *Mollicutes* genus strain nucleic acids under conditions allowing hybridization between the probe and nucleic acids in the sample to occur. Any sample potentially containing, or even suspected of containing, *Mycoplasma* or related *Mollicutes* genus strain nucleic acids may be used, including nucleic acid extracts, such as amplified or non-amplified DNA or RNA preparations. A hybridization signal from an individual address on the array indicates that the probe hybridizes to a nucleotide within the sample. This system permits the simultaneous analysis of a sample by plural probes and yields information identifying the *Mycoplasma* or related *Mollicutes* genus strain nucleic acids contained within the sample. In alternative embodiments, the array contains *Mycoplasma* or related *Mollicutes* genus strain nucleic acids and the array is contacted with a sample containing a probe. In any such embodiment, either the probe or the *Mycoplasma* or related *Mollicutes* genus strain nucleic acids may be labeled to facilitate detection of hybridization.

The nucleic acids may be added to an array substrate in dry or liquid form. Other compounds or substances may be added to the array as well, such as buffers, stabilizers, reagents for detecting hybridization signal, emulsifying agents, or preservatives.

In certain examples, the array includes one or more molecules or samples occurring on the array a plurality of times (twice or more) to provide an added feature to the array, such as redundant activity or to provide internal controls.

Within an array, each arrayed nucleic acid is addressable, such that its location may be reliably and consistently determined within the at least the two dimensions of the array surface. Thus, ordered arrays allow assignment of the location of each nucleic acid at the time it is placed within the array. Usually, an array map or key is provided to correlate each address with the appropriate nucleic acid. Ordered arrays are often arranged in a symmetrical grid pattern, but nucleic acids could be arranged in other patterns (for example, in radially distributed lines, a "spokes and wheel" pattern, or ordered clusters). Addressable arrays can be computer readable; a computer can be programmed to correlate a particular address on the array with information about the sample at that position, such as hybridization or binding data, including signal intensity. In some exemplary computer readable formats, the individual samples or molecules in the array are arranged regularly (for example, in a Cartesian grid pattern), which can be correlated to address information by a computer.

An address within the array may be of any suitable shape and size. In some embodiments, the nucleic acids are suspended in a liquid medium and contained within square or rectangular wells on the array substrate. However, the nucleic acids may be contained in regions that are essentially triangular, oval, circular, or irregular. The overall shape of the array itself also may vary, though in some embodiments it is substantially flat and rectangular or square in shape.

The detection arrays may vary in structure, composition, and intended functionality, and may be based on either a macroarray or a macroarray format, or a combination thereof. Such arrays can include, for example, at least 10, at least 25, at least 50, at least 100, or more addresses, usually with a single type of nucleic acid at each address. In the case of macroarrays, sophisticated equipment is usually not required to detect a hybridization signal on the array, though quantification may be assisted by standard scanning and/or quantification techniques and equipment. Thus, macroarray analysis as described herein can be carried out in most hospitals, agricultural and medical research laboratories, universities, or other institutions without the need for investment in specialized and expensive reading equipment.

Examples of substrates for the arrays disclosed herein include glass (e.g., functionalized glass), Si, Ge, GaAs, GaP, $SiO_2$, $SiN_4$, modified silicon nitrocellulose, polyvinylidene fluoride, polystyrene, polytetrafluoroethylene, polycarbonate, nylon, fiber, or combinations thereof. Array substrates can be stiff and relatively inflexible (for example glass or a supported membrane) or flexible (such as a polymer membrane). One commercially available product line suitable for probe arrays described herein is the Microlite line of MICROTITER™ plates available from Dynex Technologies UK (Middlesex, United Kingdom), such as the Microlite 1+96-well plate, or the 384 Microlite+384-well plate.

Addresses on the array should be discrete, in that hybridization signals from individual addresses can be distinguished from signals of neighboring addresses, either by the naked eye (macroarrays) or by scanning or reading by a piece of equipment or with the assistance of a microscope (microarrays).

Addresses in an array may be of a relatively large size, such as large enough to permit detection of a hybridization signal without the assistance of a microscope or other equipment. Thus, addresses may be as small as about 0.1 mm across, with a separation of about the same distance. Alternatively, addresses may be about 0.5, 1, 2, 3, 5, 7, or 10 mm across, with a separation of a similar or different distance. Larger addresses (larger than 10 mm across) are employed in certain embodiments. The overall size of the array is generally correlated with size of the addresses (for example, larger addresses will usually be found on larger arrays, while smaller addresses may be found on smaller arrays). Such a correlation is not necessary, however.

The arrays herein may be described by their densities (the number of addresses in a certain specified surface area). For macroarrays, array density may be about one address per square decimeter (or one address in a 10 cm by 10 cm region of the array substrate) to about 50 addresses per square centimeter (50 targets within a 1 cm by 1 cm region of the substrate). For microarrays, array density will usually be one or more addresses per square centimeter, for instance, about 50, about 100, about 200, about 300, about 400, about 500, about 1000, about 1500, about 2,500, or more addresses per square centimeter.

The use of the term "array" includes the arrays found in DNA microchip technology. As one, non-limiting example, the probes could be contained on a DNA microchip similar to the GENECHIP™ products and related products commercially available from Affymetrix, Inc. (Santa Clara, Calif.). Briefly, a DNA microchip is a miniaturized, high-density array of probes on a glass wafer substrate. Particular probes are selected, and photolithographic masks are designed for use in a process based on solid-phase chemical synthesis and photolithographic fabrication techniques similar to those used in the semiconductor industry. The masks are used to isolate chip exposure sites, and probes are chemically synthesized at these sites, with each probe in an identified location within the array. After fabrication, the array is ready for hybridization. The probe or the nucleic acid within the sample may be labeled, such as with a fluorescent label and, after hybridization, the hybridization signals may be detected and analyzed.

Kits

"Kit" as used herein refers to a combination of reagents usually formulated with necessary buffers, salts and stabilizers, where the reagents are premeasured so as to at least substantially optimize the performance of the detection method. One aspect of the invention provides for the use of a test kit to detect the presence of Mycoplasma or related Mollicutes genus strain nucleic acid in a sample. In one embodiment, the kit includes at least two different oligonucleotide primers which hybridize to the 16S-23S ribosomal RNA intergenic regions of Mycoplasma and related Mollicutes genus. The kit further comprises a positive control. In embodiments, a Mycoplasma or related Mollicutes genus strain nucleic acid detection kit for detecting the presence of Mycoplasma or related Mollicutes genus strain nucleic acid contamination comprises two or more oligonucleotide wherein each oligonucleotide is substantially complementary to a portion of a hybridize to the 16S-23S ribosomal RNA intergenic regions of Mycoplasma and related Mollicutes genus. In a preferred embodiment, the kit comprises one or more primers of each of an isolated nucleic acid specific for at least 5 consecutive nucleic acids of the 16S-23S ribosomal intergenic regions of Mycoplasma and related Mollicutes genus strains in either the 5' to 3' or 3' to 5' directions. In some embodiments, the isolated nucleic acid comprises at least five nucleic acids. In some embodiments, the isolated nucleic acid comprises a sequence identity of at least about 50% to about 99.99% to a portion of the 16S-23S ribosomal RNA intergenic regions of Mycoplasma and related Mollicutes genus strains in either the 5' to 3' or 3' to 5' directions. In a preferred embodiment, the kit comprises one or more primers of each of SEQ ID NOS: 1 to 15.

In other embodiments, the isolated nucleic acids comprise one or more mutations, variants, substitutions, analogs, deletions or combinations thereof. In some embodiments the isolated nucleic acid comprises at least one or combinations thereof, of adenine, guanine, thymine, cytosine, uracil, purine, xanthine, diaminopurine, 8-oxo-$N^6$-methyladenine, 7-deazaxanthine, 7-deazaguanine, $N^4,N^4$-ethanocytosin, $N^6,N^6$-ethano-2,6-diaminopurine, 5-methylcytosine, 5-($C^3$-$C^6$)-alkynylcytosine, 5-fluorouracil, 5-bromouracil, pseudoisocytosine, 2-hydroxy-5-methyl-4-triazolopyridin, isocytosine, isoguanin, inosine, non-naturally occurring nucleobases, locked nucleic acids (LNA), or peptide nucleic acids (PNA).

These primers can be used in real time PCR assays for the detection of Mycoplasma. In a real time PCR assay a positive reaction is detected by accumulation of a fluorescent signal. The Ct (cycle threshold) is defined as the number of cycles required for the fluorescent signal to cross the threshold (i.e. exceeds background level). Ct levels are inversely proportional to the amount of target nucleic acid in the sample (i.e. the lower the Ct level the greater the amount of target nucleic acid in the sample).

The kit may also comprise buffers, dNTPs, polymerase, dyes or detectable labels, molecular biology grade water for use as a negative control. The kit of the invention may further include a cell lysis diluent that may include water treated with diethylpyrocarbonate (DEPC) at a concentration sufficient to inactivate RNase, RNase-free Trizma hydrochloride (Tris[hydroxymethyl]aminomethane hydrochloride), Trizma base (Tris[hydroxymethyl]aminomethane), calcium chloride dihydrate, and proteinase K.

Optionally, the kit can further comprise instructions for suitable operational parameters in the form of a label or a separate insert. For example, the kit may have standard instructions informing a laboratory technician to prepare the samples for PCR.

The invention has been described in detail with reference to preferred embodiments thereof. However, it will be appreciated that those skilled in the art, upon consideration of this disclosure, may make modifications and improvements within the spirit and scope of the invention. The following non-limiting examples are illustrative of the invention.

All documents mentioned herein are incorporated herein by reference. All publications and patent documents cited in this application are incorporated by reference for all purposes to the same extent as if each individual publication or patent document were so individually denoted. By their citation of various references in this document, Applicants do not admit any particular reference is "prior art" to their invention.

EXAMPLES

Materials and Methods

Sample Preparation:

1 ml of cell culture supernatant is transferred into a sterile reaction tube (2 ml tube). The sample is centrifuged at 250×g briefly so as to pellet the cellular debris. The supernatant is then transferred into a fresh sterile tube and centrifuged at 15.000×g for 10 minutes to pellet Mycoplasma. The supernatant is carefully discarded and the pellet is re-suspended into 50 µl of Lysis Buffer. The sample is vortexed and heated to 95° C. for 5 minutes. Up to 12 µl per reaction of this solution is used to test for Mycoplasma contamination or it can be stored at −20° C. for later use.

In order to build the High Melting Positive Control (a discriminatory positive control), each one of the following nucleotides sequences was cloned into a standard cloning vector (No mater of their orientation: sense or antisense).

High Melting Positive Control Sequences

SEQ ID No 1
```
GTCACACCAT GGGAGCTGGT AACCGCCCGG CGTGGGCGGT GCCACCCCTC CCCGTAACAA GGTATCCCTA CGAGAAC
CAGTGTGGTA CCCTCGACCA TTGGCGGGCC GCACCCGCCA CGGTGGGGAG GGGCATTGTT CCATAGGGAT GCTCTTG
```

SEQ ID No 2
```
GTCACACCAT GGGAGCTGGT AACGTGGCCG CCCGGCGTGG GCGGTGCCAC CCCTCCCGCC GGCGTAACAA GGTATCCCTA CGAGAAC
CAGTGTGGTA CCCTCGACCA TTGCACCGGC GGGCCGCACC CGCCACGGTG GGGAGGGCGG CCGCATTGTT CCATAGGGAT GCTCTTG
```

SEQ ID No 3
```
GTCACACCAT GGGAGCTGGT AACCCTTCGT GGCCGCCCGG CGTGGGCGGT GCCACCCCTC CCGCCGGCGG CCCGTAACAA GGTATCCCTA
CGAGAAC
```

```
                                                          -continued
CAGTGTGGTA CCCTCGACCA TTGGGAAGCA CCGGCGGGCC GCACCCGCCA CGGTGGGGAG GGCGGCCGCC GGGCATTGTT CCATAGGGAT
GCTCTTG SEQ ID No 4
GTCACACCAT GGGAGCTGGT AACCGCCCGG CGTGGGCGGT GCCACCCCTC CCCCGGCGT AACAAGGTAT CCCTACGAGA AC
CAGTGTGGTA CCCTCGACCA TTGGCGGGCC GCACCCGCCA CGGTGGGGAG GGGGGCCGCA TTGTTCCATA GGGATGCTCT TG SEQ ID No 5
GTCACACCAT GGGAGCTGGT AACCGCCCGG CGTGGGCGGT GCCACCCCTC CCCCGGCGG CCCGTAACAA GGTATCCCTA CGAGAAC
CAGTGTGGTA CCCTCGACCA TTGGCGGGCC GCACCCGCCA CGGTGGGGAG GGGGGCCGCC GGGCATTGTT CCATAGGGAT GCTCTTG SEQ ID No 6
GTCACACCAT GGGAGCTGGT AACGTGGCCG CCCGGCGTGG GCGGTGCCAC CCCTCCCCGT AACAAGGTAT CCCTACGAGA AC
CAGTGTGGTA CCCTCGACCA TTGCACCGGC GGGCCGCACC CGCCACGGTG GGGAGGGGCA TTGTTCCATA GGGATGCTCT TG SEQ ID No 7
GTCACACCAT GGGAGCTGGT AACGTGGCCG CCCGGCGTGG GCGGTGCCAC CCCTCCCCCC GGCGGCCCGT AACAAGGTAT CCCTACGAGA
AC
CAGTGTGGTA CCCTCGACCA TTGCACCGGC GGGCCGCACC CGCCACGGTG GGGAGGGGGG CCGCCGGGCA TTGTTCCATA GGGATGCTCT
TG SEQ ID No 8
GTCACACCAT GGGAGCTGGT AACCCTTCGT GGCCGCCCGG CGTGGGCGGT GCCACCCCTC CCCCGGCGT AACAAGGTAT CCCTACGAGA
AC
CAGTGTGGTA CCCTCGACCA TTGGGAAGCA CCGGCGGGCC GCACCCGCCA CGGTGGGGAG GGGGCCGCA TTGTTCCATA GGGATGCTCT
TG SEQ ID No 9
GTCACACCAT GGGAGCTGGT AACCCTTCGT GGCCGCCCGG CGTGGGCGGT GCCACCCCTC CCGTAACAA GGTATCCCTA CGAGAAC
CAGTGTGGTA CCCTCGACCA TTGGGAAGCA CCGGCGGGCC GCACCCGCCA CGGTGGGGAG GGGCATTGTT CCATAGGGAT GCTCTTG
```

Forward Primers:
```
  Seq
  ID NOS:
     10   5' GTC AMA CCA TGG GAG YTG GTA A 3'
     11   5' CAA ACC ACG AAA GTG GGC AA 3'
     12   5' CCC GTC AAA CTA CGA GAG GTA AGT A 3'
     13   5' CCG TCA CAC CAT GAG AGT TGA TAA 3'
     14   5' CCG TCA AAC TAT GAA AGC TGG TAA 3'
```
Reverse Primers:
```
                                       SEQ ID NO: 15
5' GTT CTC GTA GGG RTA CCT TGT TAC G 3'
```

Setting up the Experiment on a Real Time PCR Device: The thermal-cycling conditions are set as indicated in the table below. The sample volume is set at 30 rd.

| | Steps | | | |
|---|---|---|---|---|
| Hot Start Polymerase Activation | PCR 40 Cycles | | | Dissociation Melt curve Add Dissociation |
| Hold | Denature | Anneal | Extend | Stage |
| Temp 95° C. | 95° C. | 55° C. | 60° C. | (*) |
| Time 10 min | 15 sec | 15 sec | 1 min | |

* Add Dissociation Stage-specific details are found in the user's Real-Time PCR System instruction manuals.

Kit Reagents and Premix Solutions:

All kit reagents are thawed completely and kept at 4° C. throughout the experiment. The reagents are vortexed and spun down. The premixed solution is prepared according to the following table:

| Premix Solution Component | Volume for one reaction (µl) | Volume for four reactions (µl) * |
|---|---|---|
| SYBR Green PCR Master Mix 2x | 15 | 66 |
| 10X Primer Solution | 3.0 | 13.2 |
| Final premix volume | 18 | 79.2 |

* 10% excess to compensate for pipetting errors.

The premix solution is then mixed by gently pipetting up and down.

The PCR reactions are prepared as follows:

| | Reaction | Each Tube |
|---|---|---|
| − | Negative control reaction | 18 µl of Premix Solution<br>12 µl of Negative Control (Water) |
| ? | Unknown sample reaction | 18 µl of Premix solution<br>10 µl of unknown sample (up to 12 µl)<br>2 µl of water (up to a final volume of 30 µl) |
| \ | Inhibition control reaction | 18 µl of Premix Solution<br>10 µl of unknown sample<br>2 µl of Discriminatory Positive Control (DPC) |
| + | Positive control reaction | 18 µl of Premix Solution<br>2 µl of Discriminatory Positive Control (DPC)<br>10 µl of water |

The reactions are performed in a real-time PCR system.

Test Sample:

The table below shows the criteria for positive and negative calls. A positive call indicates that at least one genome copy of *Mycoplasma* DNA was present in the test reaction and the sample is positive for the presence of *Mycoplasma*.

Criteria for test sample:

| Result | Ct | Tm |
|---|---|---|
| *Mycoplasma* Positive Sample | ≤36 | 75° C.-85° C. |
| *Mycoplasma* Negative Sample | ≥36 | 75° C.-85° C. |

Criteria for controls:

| Result | Ct | Tm |
|---|---|---|
| Discriminatory Positive Control (DPC) | 25-28 | >85° C. |
| Negative Control | ≥36 | <75° C. |
| Inhibition Control (Test Sample plus DPC) | Non less than 3 Ct value comparing to DPC Ct value | Both pikes (DPC + Sample) |

Specificity:

Laboratory tests and bioinformatics analysis of the 16S-23S ribosomal RNA intergenic spacer regions form the following *Mycoplasma* and related *Mollicutes* genus were detected.

*Acholeplasma laidlawii* ATCC23206; *Spiroplasma citri* ATCC27556; *M. arginini* ATCC23838; *M. arthritidis* ATCC19611; *M. bovis* ATCC25025; *M. capricolum capricolum* ATCC27343; *M. fermentans* ATCC49892; *M. gallisepticum* ATCC19610; *M. genitalium* ATCC33530; *M. hominis* ATCC27545; *M. hyopneumoniae* ATCC25934; *M. orale* ATCC23714; *M. pirum* ATCC25960; *M. pneumoniae* ATCC15531; *M. pulmonis* GenBank X58554; *M. salivarium* ATCC23064; *M. synoviae* ATCC25204; *M. mirounga* GenBank GU905026; *M. adleri* strain G145; *M. agalactiae* strainGO-5; *M. agassizii* strain PS6; *M. alkalescens* ATCC29103; *M. alligatoris* ATCC700619; *M. alvi* strain Ilsley; *M. amphoriforme* strain A39; *M. anseris* strain 1219; *M. auris* strain UTA; *M. bovigenitalium* strain PG-11; *M. bovirhinis* ATCC27748; *M. bovoculi* ATCC29104; *M. buccale* ATCC23636; *M. buteonis* strain Bb/T2g; *M. californicum* strain ST6; *M. canadense* strain 466; *M. canimucosale* type strain 1642; *M. canis* ATCC19525; *M. caviae* strain ATCC27108; *M. cavipharyngis* ATCC43016; *M. citelli* strain RG2C; *M. cloacale* strain 383; *M. collis* ATCC35278; *M. columbinasale* ATCC33549; *M. columbinum* strain FG295; *M. columborale* ATCC29258; *M. conjunctivae* Goat655; *M. corogypsi* strain BV1-5; *M. cottewii* ATCC43093; *M. cricetuli* ATCC35279; *M. crocodyli* ATCC51981; *M. cynos* strain H381; *M. dispar* ATCC27140; *M. edwardii* strain 04-3440; *M. elephantis* ATCC51980; *M. equigenitalium* ATCC29869; *M. equirhinis* ATCC29420; *M. falconis* ATCC51372; *M. fastidiosum* ATCC33229; *M. fauciunz* ATCC25293; *M. feliminutum* ATCC25749; *M. felis* GenBank AF443608; *M. flocculare* strain Ms42; *M. gallinarum* strain B2Dinter; *M. gallisepticum* GenBank FJ468427; *M. gallopavonis* ATCC33551; *M. glycophilum* ATCC35277; *M. gypis* ATCC51370; *M. hyopharyngis* strain H36B-F; *M. hyorhinis* ATCC29052; *M. iguanae* strain 2327; *M. indiense* ATCC51125; *M. iners* ATCC15969; *M. iowae* ATCC33552; *M. lagogenitalium* ATCC700289; *M. leachii* strain PG50; *M. leonicaptivi* ATCC49890; *M. leopharyngis* ATCC49889; *M. lipofaciens* ATCC35015; *M. lipophilum* ATCC27104; *M. maculosum* strain PG15; *M. meleagridis* ATCC27764; *M. microti* strain IL371; *M. moatsii* strain MK405; *M. mobile* ATCC43663; *M. molare* strain H542; *M. muris* ATCC33757; *M. mustelae* ATCC35214; *M. neurolyticum* ATCC19988; *M. opalescens* strain MHS408; *M. ovipneumoniae* ATCC29419; *M. oxoniensis* ATCC49694; *M. phocicerebrale* strain CSL5195S2; *M. phocirhinis* strain CSL7475-4; *M. primatum* strain HRC292; *M. pullorum* ATCC33553; *M. putrefaciens* ATCC33756; *M. simbae* ATCC49888; *M. spermatophilum* strain AH159; *M. sphenisci* strain UCMJ; *M. spumans* ATCC19526; *M. sturni* ATCC51945; *M. sualvi* ATCC33004; *M. subdolum* ATCC29870; *M. testudineum* ATCC700618; *M. testudinis* ATCC43263; *M. verecundum* ATCC27862; *M. vulturii* strain Gb-V33; *M. yeatsii* ATCC43094; *M. zalophi* strain CSL5195; *M. zalophidermidis* strain CSL4779.

There was no amplification of genomic human, mouse, CHO-S cell line (Invitrogen Corporation, 1600 Faraday Avenue, Carlsbad, Calif. 92008) or chromosomal *E. coli* DNAs using the primers for detecting *Mycoplasma*.

In addition, bioinformatics analysis excluded the possibility of cross reaction with the following species:

*Bacillus cereus* ATCC53522; *Bacillus subtilis* ATCC6051; *Campylobacter jejuni* ATCC33250; *Chlamydophila pneumoniae* ATCC VR-2282; *Citrobacter freundii* ATCC 8090; *Clostridium perfringens* ATCC10543; *Enterobacter aerogenes* ATCC 13048; *Enterococcus faecalis* ATCC19433; *Escherichia coli* strain 0157:H7; *Klebsiella oxytoca* ATCC13182T; *Lactobacillus delbrueckii* subsp. *bulgaricus* ATCC 11842; *Listeria monocytogenes* ATCC35152; *Pseudomonas aeruginosa* ATCC28853; *Shigella dysenteriae* strain GYPB22; *Staphylococcus aureus* ATCC29740; *Vibrio cholerae* ATCC14035; *Yersinia enterocolitica* subsp. *enterocolitica* ATCC 9610.

What is claimed is:

1. A *Mycoplasma* detection kit comprising at least one synthetic oligonucleotide selected from the group consisting of SEQ ID NOS: 10, 12, 13, 14, 15, and sequences complementary thereto; a buffer; a discriminatory positive control synthetic oligonucleotide (DPC), wherein the DPC comprises at least one sequence selected from the group consisting of SEQ ID NOS: 4 and 6; and an instruction for operation.

2. The kit of claim 1 comprising two or more synthetic oligonucleotides of claim 1 comprising a nucleic acid having at least 95% sequence identity or complementarity with either strand in the sense or anti-sense orientation of a sequence selected from the group consisting of SEQ ID NOS: 1 to 10 and 12 to 15.

3. A *Mycoplasma* detection kit comprising at least one synthetic oligonucleotide selected from the group consisting of SEQ ID NOS: 10, 12, 13, 14, 15, and sequences complementary thereto; a buffer; a discriminatory positive control synthetic oligonucleotide (DPC), wherein a detectable label is attached at a 5'-end or a 3'-end of the synthetic oligonucleotide and the detectable label is selected from the group consisting of a fluorophore, a chromophore, a luminescent compound, a radioactive isotope, an enzyme substrate, a co-factor, a ligand, a hapten, an enzyme, a magnetic particle and a barcode, wherein the DPC comprises at least one sequence selected from the group consisting of SEQ ID NOS: 4 and 6; and an instruction for operation.

4. The kit of claim 3 comprising two or more synthetic oligonucleotides of claim 1.

5. A *Mycoplasma* detection kit comprising:

at least one synthetic oligonucleotide comprising a nucleic acid sequence selected from the group consisting of SEQ ID NOS: 10, 12, 13, 14, 15, and sequences complementary thereto;

a lysis buffer;

a solution including a buffer, a dye, dNTPs, and a polymerase;

a discriminatory positive control synthetic oligonucleotide (DPC), wherein the DPC comprises at least one sequence selected from the group consisting of SEQ ID NOS: 4 and 6; and an instruction for operation.

6. The kit of claim 5, wherein the two or more synthetic oligonucleotides include at least one forward primer and at least one reverse primer.

7. The kit of claim 5, wherein the dye comprises at least one selected from the group consisting of SYBR green and ROX.

* * * * *

SEQUENCE LISTING

```
<160> NUMBER OF SEQ ID NOS: 15

<210> SEQ ID NO 1
<211> LENGTH: 154
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
gtcacaccat gggagctggt aaccgcccgg cgtgggcggt gccaccctc cccgtaacaa      60 ggtatcccta cgagaaccag tgtggtaccc tcgaccattg gcgggccgca cccgccacgg     120
tggggagggg cattgttcca tagggatgct cttg                                 154
```

<210> SEQ ID NO 2
<211> LENGTH: 174
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
gtcacaccat gggagctggt aacgtggccg cccggcgtgg gcggtgccac ccctcccgcc     60
ggcgtaacaa ggtatcccta cgagaaccag tgtggtaccc tcgaccattg caccggcggg    120
ccgcacccgc cacggtgggg agggcggccg cattgttcca tagggatgct cttg           174

<210> SEQ ID NO 3
<211> LENGTH: 194
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
gtcacaccat gggagctggt aacccttcgt ggccgcccgg cgtgggcggt gccacccctc     60
ccgccggcgg cccgtaacaa ggtatcccta cgagaaccag tgtggtaccc tcgaccattg    120
ggaagcaccg gcgggccgca cccgccacgg tggggagggc ggccgccggg cattgttcca    180
tagggatgct cttg                                                      194

<210> SEQ ID NO 4
<211> LENGTH: 164
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
gtcacaccat gggagctggt aaccgcccgg cgtgggcggt gccacccctc ccccggcgt      60 aacaaggtat ccctacgaga accagtgtgg taccctcgac cattggcggg ccgcacccgc    120
cacggtgggg aggggggccg cattgttcca tagggatgct cttg                      164

<210> SEQ ID NO 5
<211> LENGTH: 174
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
gtcacaccat gggagctggt aaccgcccgg cgtgggcggt gccacccctc ccccggcgg      60 cccgtaacaa ggtatcccta cgagaaccag tgtggtaccc tcgaccattg gcggccgca    120 cccgccacgg tggggagggg ggccgccggg cattgttcca tagggatgct cttg           174

<210> SEQ ID NO 6
<211> LENGTH: 164
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6

```
gtcacaccat gggagctggt aacgtggccg cccggcgtgg gcggtgccac ccctccccgt    60
aacaaggtat ccctacgaga accagtgtgg taccctcgac cattgcaccg gcgggccgca   120
cccgccacgg tggggagggg cattgttcca tagggatgct cttg                    164
```

<210> SEQ ID NO 7
<211> LENGTH: 184
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7

```
gtcacaccat gggagctggt aacgtggccg cccggcgtgg gcggtgccac ccctccccc    60
ggcggcccgt aacaaggtat ccctacgaga accagtgtgg taccctcgac cattgcaccg   120
gcgggccgca cccgccacgg tggggagggg gccgccggg cattgttcca tagggatgct   180
cttg                                                                184
```

<210> SEQ ID NO 8
<211> LENGTH: 184
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8

```
gtcacaccat gggagctggt aaccctttcgt ggccgcccgg cgtgggcggt gccacccctc    60
cccccggcgt aacaaggtat ccctacgaga accagtgtgg taccctcgac cattgggaag   120
caccggcggg ccgcacccgc cacggtgggg agggggccg cattgttcca tagggatgct   180
cttg                                                                184
```

<210> SEQ ID NO 9
<211> LENGTH: 174
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9

```
gtcacaccat gggagctggt aacccttcgt ggccgcccgg cgtgggcggt gccacccctc    60
cccgtaacaa ggtatcccta cgagaaccag tgtggtaccc tcgaccattg gaagcaccg   120
gcgggccgca cccgccacgg tggggagggg cattgttcca tagggatgct cttg         174
```

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10

```
gtcamaccat gggagytggt aa                                             22
```

<210> SEQ ID NO 11

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
caaaccacga aagtgggcaa                                              20

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
cccgtcaaac tacgagaggt aagta                                        25

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ccgtcacacc atgagagttg ataa                                         24

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ccgtcaaact atgaaagctg gtaa                                         24

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gttctcgtag ggrtaccttg ttacg                                        25
```